(12) United States Patent
Zhang et al.

(10) Patent No.: US 10,896,739 B2
(45) Date of Patent: *Jan. 19, 2021

(54) CIRCADIAN PHASE ESTIMATION, MODELING AND CONTROL

(71) Applicant: Rensselaer Polytechnic Institute, Troy, NY (US)

(72) Inventors: Jiaxiang Zhang, Painted Post, NY (US); John T. Wen, Melrose, NY (US); Agung Julius, Poestenkill, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/689,283

(22) Filed: Nov. 20, 2019

(65) Prior Publication Data
US 2020/0090781 A1    Mar. 19, 2020

Related U.S. Application Data

(63) Continuation of application No. 14/405,973, filed as application No. PCT/US2013/044007 on Jun. 4, 2013, now Pat. No. 10,529,440.

(Continued)

(51) Int. Cl.
*A61N 5/01* (2006.01)
*G16B 5/00* (2019.01)
(Continued)

(52) U.S. Cl.
CPC .............. *G16B 5/00* (2019.02); *A61B 5/4857* (2013.01); *A61N 5/0618* (2013.01); *G06N 7/02* (2013.01);
(Continued)

(58) Field of Classification Search
CPC ........ G16B 5/00; G16H 50/50; A61B 5/4857; A61N 5/0618; A61N 2005/0626; G06N 7/02; Y02A 90/10
See application file for complete search history.

(56) References Cited

U.S. PATENT DOCUMENTS

2005/0015122 A1* 1/2005 Mott ................... H05B 47/105
                                                                    607/88
2014/0160569 A1* 6/2014 Blair ...................... G02C 7/104
                                                                    359/589

OTHER PUBLICATIONS

Shaw Youngstedt "Circadian phase-shifting effects of a laboratory environment: a clinical trial with bright and dim light" (Year: 2005).*

* cited by examiner

*Primary Examiner* — Doon Y Chow
*Assistant Examiner* — Abdou K Seye
(74) *Attorney, Agent, or Firm* — Murtha Cullina LLP; Anthony P. Gangemi

(57) ABSTRACT

Method, system and computer program product are provided for estimating a circadian phase of a subject by: obtaining a sensed biological signal for the subject; and using, by one or more processors, adaptive frequency tracking to adaptively estimate the circadian phase of the subject from the sensed biological signal. Circadian phase estimation may be accelerated by providing a feedback loop for the adaptive frequency tracking, which utilizes, in part, a circadian phase model in automatically ascertaining a phase correction for the adaptive frequency tracking. The circadian phase estimation may be used in automatically constructing a light-based circadian rhythm model for the subject using a linear parameter-varying (LPV) formulation, and once constructed, the circadian rhythm model for the subject may be used to provide light-based circadian rhythm regulation.

20 Claims, 20 Drawing Sheets

Related U.S. Application Data

(60) Provisional application No. 61/689,391, filed on Jun. 5, 2012.

(51) Int. Cl.
    *A61N 5/06*          (2006.01)
    *A61B 5/00*          (2006.01)
    *G16H 50/50*        (2018.01)
    *G06N 7/02*          (2006.01)

(52) U.S. Cl.
    CPC ..... *G16H 50/50* (2018.01); *A61N 2005/0626* (2013.01); *Y02A 90/10* (2018.01)

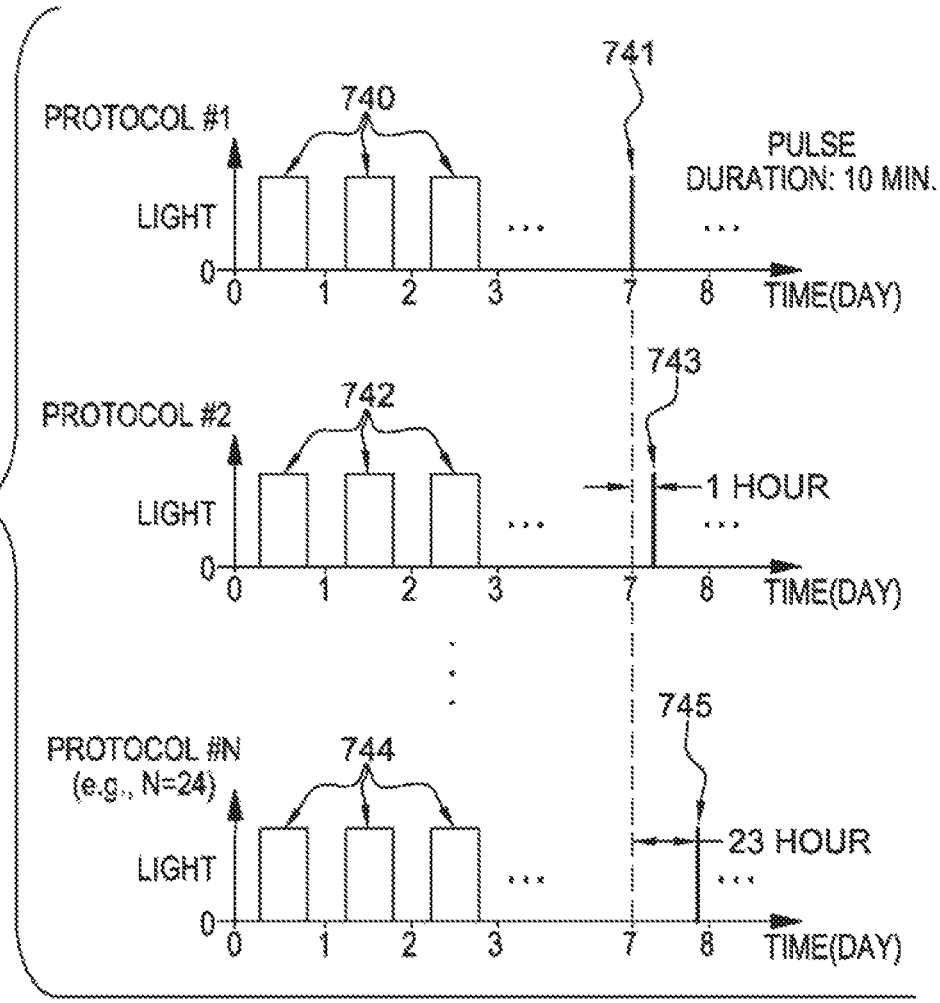

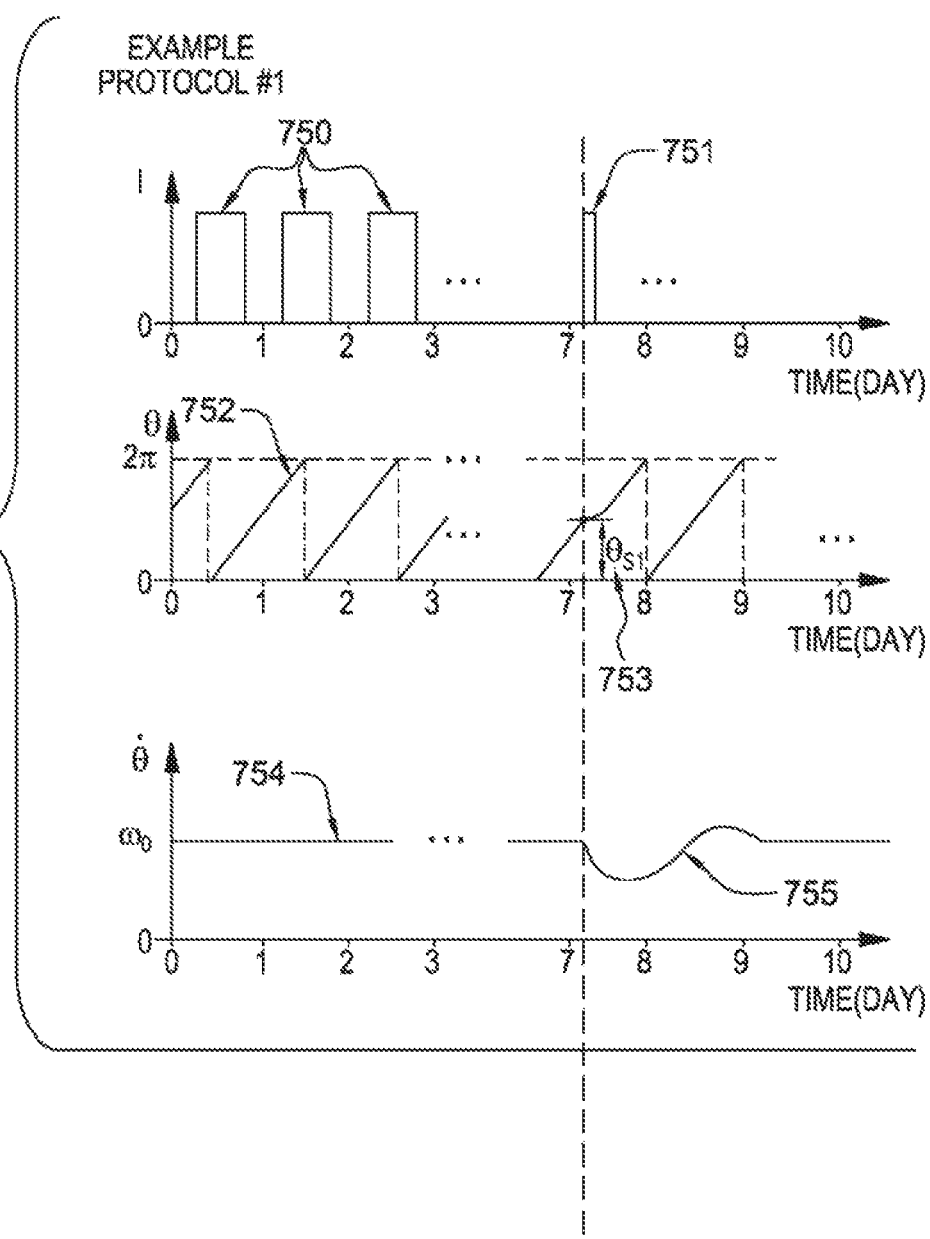

CIRCADIAN PHASE ESTIMATION, MODELING AND CONTROL

CROSS-REFERENCE TO RELATED APPLICATION

This application is a continuation of U.S. Utility patent application Ser. No. 14/405,973, filed Dec. 5, 2014, now patent Ser. No. 10/529,440, which is a national stage filing of International Application No. PCT/US2013/044007, filed on Jun. 4, 2013, which claims the benefit of U.S. provisional patent application Ser. No. 61/689,391, filed Jun. 5, 2012, which are hereby incorporated herein by reference in their entireties.

STATEMENT REGARDING FEDERALLY SPONSORED RESEARCH AND DEVELOPMENT

The following invention was made with government support under: Contract No. EEC0812056, awarded by the National Science Foundation. The Government has certain rights in this invention.

BACKGROUND

All species on the planet, including humans, are exposed to 24-hour patterns of light and darkness as the Earth rotates on its axis. In response to these natural light-dark patterns, species have evolved biological rhythms known as circadian rhythms that repeat approximately every 24 hours. Examples of circadian rhythms include oscillation in core body temperature, hormone secretion, sleep, and alertness. Circadian oscillations occur at the cellular level, including cell mitosis and DNA repair. In mammals, the central circadian pacemaker is located in the suprachiasmatic nuclei (SCN) of the brain's hypothalamus. This master clock provides timing cues throughout the body to regulate the diverse physiological, hormonal and behavioral circadian rhythms. The timing of the circadian pacemaker in humans is slightly longer than 24 hours, so the exogenous light-dark pattern (i.e. natural light-dark pattern caused by the Earth's rotation) resets the timing of the SCN every day as seasons change or as we travel. In this way, our internal clock can be synchronized with the local solar time anywhere on the planet. A breakdown in the synchrony between the circadian pacemaker and the local solar time (as can occur with travel), will disrupt sleep, digestion, alertness, and in chronic cases, research suggests may cause cardiovascular anomalies and/or accelerated cancerous tumor growth.

As an example, epidemiological studies have shown that rotating-shift nurses, who experience a marked lack of synchrony between rest-activity patterns and light-dark cycles, are at higher risk for breast cancer compared with day-shift nurses. More specifically, environmental factors such as electric light at night (LAN) have been implicated as agents in endocrine disruption. It is hypothesized that LAN suppresses pineal melatonin production by the pineal gland, which may shift rest-activity patterns, making them asynchronous with the solar day/night cycle. It has also been shown that melatonin is an antioxidant, significantly retarding the growth of breast cancer and other tumors. In fact, it probably plays a significant role in the development of cancer in mammals. Moreover, in addition to heightened cancer risks, other diseases have been associated with night-shift work, such as diabetes and obesity, which suggests a role of circadian disruption in the development and progression of such diseases.

Though many environmental stimuli have been reported to influence the central circadian pacemaker in mammals, light is established as the dominant environmental stimulus that synchronizes, or entrains, the circadian pacemaker to the local environment, e.g. the light-dark cycle. Furthermore, it is known that light must be incident on the retina to be a stimulus for the human circadian pacemaker. In 2002, a new photoreceptor in the retina was discovered, the intrinsically photosensitive retinal ganglion cell, which has direct nerve projections to the circadian pacemaker in the SCN. This discovery solidified the importance of light in affecting the circadian pacemaker and has invigorated research into light therapy for treating health issues thought to originate from circadian disruption.

The human circadian pacemaker continues to oscillate in the absence of environmental stimuli, but with a free running period slightly different than 24 hrs. In humans, the average free running period is approximately 24.2 hrs. Depending on when light is applied over the course of 24 hrs, it can advance, delay, or have very little effect on the phase of an individual's circadian pacemaker. For instance, light applied before the body reaches its minimum core body temperature will delay the phase of the pacemaker while light applied after the body reaches its minimum core body temperature will advance the phase of the circadian pacemaker. Since the human circadian pacemaker is, on average, slightly longer than 24 hrs, humans generally need morning light to maintain synchronization (or entrainment) between the circadian pacemaker and the local time.

A mathematical model was developed by Kronauer and others that predicts the effect of light on the human circadian pacemaker. The human circadian pacemaker may be modeled as a Van der Pol type limit-cycle oscillator with a nonlinear light dependent driving force. Simulating the behavior of the circadian pacemaker for various light input patterns can be done by numerically solving the set of differential equations that describe the oscillator.

The phase of the circadian pacemaker rhythm may be assessed, in one aspect, by measuring the concentration of proteins that participate in circadian rhythm regulation. For humans, certain hormones related to circadian rhythm such as melatonin, cortisol, alpha amyloid, have also been used as circadian rhythm markers. These types of direct measurements are intrusive in terms of measurements (blood serum, saliva) and time consuming and expensive in terms of analysis. As a result, the sampling rate is very low, at best once per several hours, over limited duration during experimental trials. Much more desirable is the use of indirect markers, such as body temperature, heart/pulse rate, activity level, etc. However, these type of markers or biological signals are "masked" by other factors, e.g., light stimulates activity response via visual pathway in addition to the circadian pathway, environmental conditions could affect body temperature as well as heart rate, etc. There are numerous methods that estimate circadian phase based on measured biomarkers. Most of these methods are batch-based, meaning that the circadian rhythm is extracted in post-processing after the signal has been completely obtained. For instance, the techniques may include the manual inspection of actogram, statistical method, Fourier analysis, cosinor, and activity onset.

BRIEF SUMMARY OF THE INVENTION

In accordance with one or more aspects of the present invention, a method is provided which includes estimating a circadian phase of a subject by: obtaining a sensed biological signal for the subject; and using, by one or more processors, adaptive frequency tracking to adaptively estimate the circadian phase of the subject from the sensed biological signal of the subject.

In another aspect, a method is provided which includes ascertaining a light-based circadian rhythm model for a subject. The ascertaining includes: obtaining biological data from a subject and estimating therefrom circadian phase of the subject; sensing circadian light intensity exposure of the subject commensurate with obtaining the biological data; and using, by one or more processors, a linear parameter-varying system formulation with the sensed circadian light as input and the estimated circadian phase of the subject as output to ascertain the light-based circadian rhythm model.

In yet another aspect, a system is provided which includes a data processing system for facilitating estimating a circadian phase of a subject, the data processing system including one or more processors to perform: obtaining a sensed biological signal for the subject; and using, by the one or more processors, adaptive frequency tracking to adaptively estimate the circadian phase of the subject from the sensed biological signal.

In a further aspect, a computer program product is provided for adaptively estimating circadian phase of a subject. The computer program product includes a computer-readable storage medium readable by one or more processors and storing instructions for execution by the one or more processors for performing a method comprising: obtaining a sensed biological signal for the subject; and using adaptive frequency tracking to adaptively estimate the circadian phase of the subject from the sensed biological signal.

Additional features and advantages are realized through the techniques of the present invention. Other embodiments and aspects of the invention are described in detail herein and are considered a part of the claimed invention.

BRIEF DESCRIPTION OF THE SEVERAL VIEWS OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

FIG. 7C depicts one embodiment of different lighting profiles or protocols for use in light-based circadian rhythm model construction, in accordance with, for instance, the processing of FIGS. 7A & 7B, in accordance with one or more aspects of the present invention;

FIG. 7D illustrates circadian phase response and time-derivative response of the circadian phase, based on application of a sample circadian light profile to the subject, in accordance with one or more aspects of the present invention;

DETAILED DESCRIPTION

Figure 1:
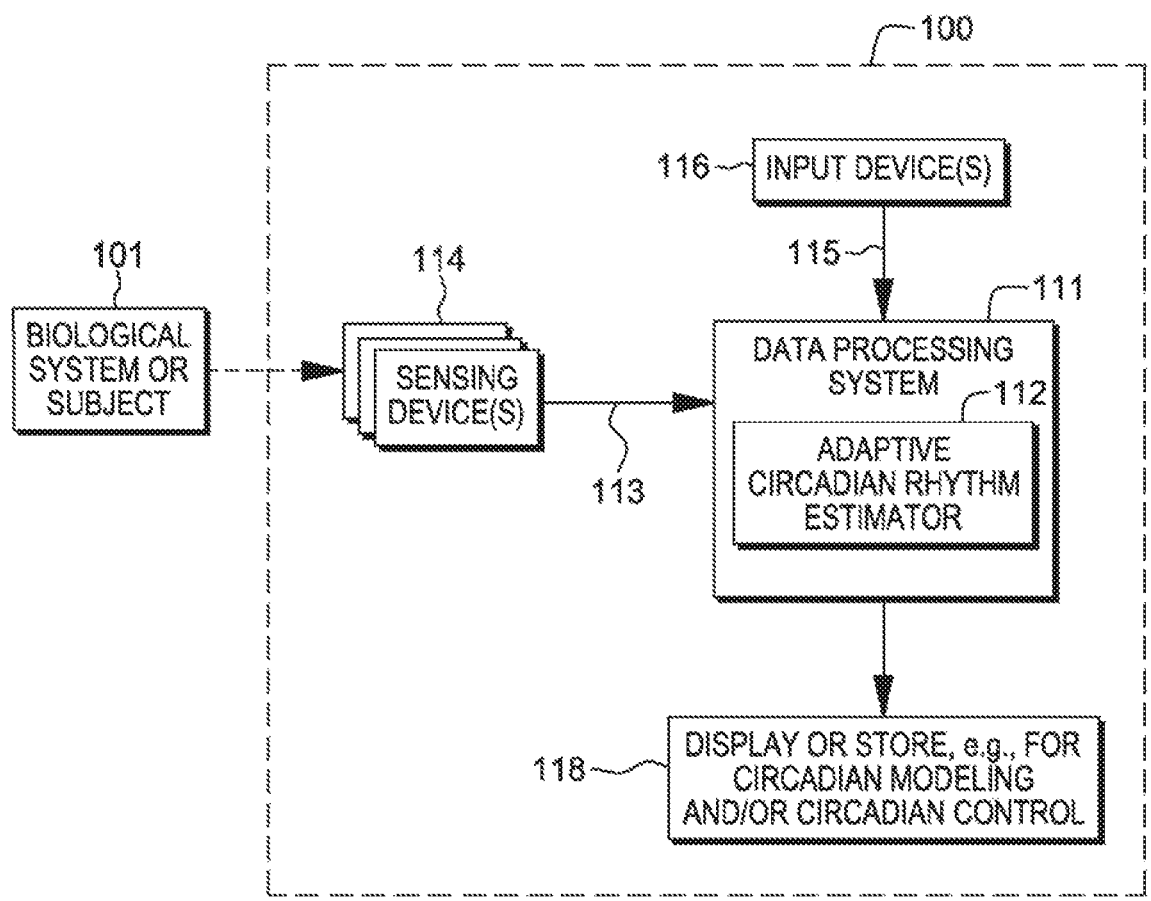
FIG. 1 illustrates one embodiment of a system for facilitating estimating circadian phase of a subject, and for instance, for generating a circadian rhythm model based thereon, in accordance with one or more aspects of the present invention.

As briefly described above, circadian rhythm is a biological process critical to the well-being of living organisms, from plants to insects and mammals. Circadian rhythms oscillate with a period of approximately 24 hours due to the 24-hour light-darkness pattern of the solar day. Some physiological processes, such as alertness regulation and hormone production, are related to a subject's circadian rhythm. Circadian disruption, as experienced by night shift workers, travelers across multiple time zones, submariners or miners, can lead to lower productivity, sleep disorders, and more serious health problems. Light pulses, applied at correct circadian argument, can be used for circadian re-entrainment or regulation by stimulating human's non-visual pathway. In cancer treatment, chronotherapy, in which the doctors time the delivery of chemotherapy drugs based on a patient's individual circadian rhythm, helps to minimize the damage of chemotherapy to healthy tissues. By pinpointing the circadian phase that is best for treatment, higher doses can be delivered that do less harm to the rest of the body.

In one approach, phase of a circadian rhythm may be assessed by measuring the concentration of proteins that participate in circadian rhythm regulation. For humans, certain hormones related to circadian rhythm, such as melatonin, cortisol, alpha amyloid, have also been used as circadian rhythm markers. These types of direct measurements are intrusive in terms of measurements (blood serum, saliva) and time consuming and expensive in terms of analysis. As a result, the sampling rate is low, for instance, once per several hours, over limited duration during experimental trials. Much more common is the use of indirect markers, such as body temperature, heart/pulse rate, activity level, etc. However, these signals are "masked" by other factors, e.g., light stimulates activity response via visual pathway in addition to the circadian pathway, environmental conditions could affect body temperature as well as heart rate, etc. There are numerous methods that estimate circadian phase based on measured biomarkers. Most of the methods are batch-based, meaning that the circadian rhythm is extracted in post-processing after the signal has been completely obtained. These techniques include the manual inspection of actogram, statistical method, Fourier analysis, cosinor, and activity onset.

Various groups have proposed the use of light to entrain the circadian rhythm. Many of these methods are based on the phase response curve (PRC), which is the amount of phase shift due to a specified light pulse input at different points of the circadian phase. Such approach is based on the steady state phase response and does not take into account the transient. This means there is no guaranteed entrainment time. Several methods use a dynamic model to capture the transient effect, but they are dependent on averaged circadian models and do not tailor to the individual subject's behavior. A closed loop strategy, i.e., adjusting light intensity based on the circadian phase, has also been suggested and demonstrated in simulation. Closed loop control is attractive as it could accommodate variations between models and disturbances from the environment. However, such schemes are still dependent on model fidelity.

Generally stated, disclosed herein are certain novel methods, systems and computer program products which facilitate estimating in real-time circadian phase of a subject, without the use of a model. The estimating includes: obtaining a sensed biological signal measured or derived from the subject; and using, by one or more processors, adaptive frequency tracking to adaptively estimate the circadian phase of the subject from the individual subject's sensed biological signal. In another aspect, acceleration of estimating of the circadian phase from the sensed biological signal can be provided via a feedback loop for the adaptive frequency tracking, wherein the feedback loop utilizes, in part, a circadian phase model to automatically ascertain a phase correction from the adaptive frequency tracking, as discussed hereinbelow. Still further, the estimated circadian phase may be employed in automatically constructing an individualized light-based circadian rhythm model using, in combination with the circadian phase estimate, a corresponding circadian light exposure as input. Once constructed, the subject's individual light-based circadian rhythm model may be used in light-based circadian rhythm regulation, as discussed herein.

More particularly, the methods, systems, and computer program products disclosed herein include, in different aspects:

1. Model-free real-time adaptive circadian phase estimation. This aspect of the method is a significant improvement over the current state of the art in at least the following aspects:

a. The method does not depend on any a priori model. This allows the method to be tailored to an individual circadian rhythm, rather than depending on a one-size-fits-all model based on an average subject response.

b. The method is adaptive. It adjusts the estimated circadian period and phase dynamically and filters measurement noise, instead of relying on a priori modeling assumptions and calibrations.

c. The method is fast. It consists of a set of recursive nonlinear filters that can be readily computed in real-time, and does not require solution of time consuming and numerically challenging nonlinear optimization(s). Compared to the moving cosinor method, a widely-used real time model-free method, the methods disclosed herein reduce the convergence time by a factor of two.

The inventive process is based on adaptive frequency tracking. A particular implementation may utilize an adaptive notch filter (ANF), but other adaptive frequency tracking may be used. These recursive algorithms adaptively estimate the amplitude and phase parameters, which may be time varying or imprecisely known, of a single harmonic component (a sinusoidal waveform) in the measured signal. The adaptive frequency tracking is extended herein beyond the standard single-harmonic component formulation to multiple harmonics to account for complex waveforms of noisy biological signals. The estimator disclosed herein has been tested on rat activity signals, *drosophila* locomotor activity signals, and simulated human circadian data by using several accepted circadian models. The computational efficiency and fast convergence of the adaptive frequency tracking disclosed herein makes it suitable for continuous circadian rhythm monitoring, e.g., using a wearable device. Multiple biological signals or bio-markers may also be combined in the estimator implementation disclosed.

2. Acceleration of circadian rhythm estimation. A method is disclosed herein to speed up convergence of the estimated circadian phase to its true value. This method combines the model-free adaptive circadian phase estimator (above) with a model-based circadian phase computation based on circadian rhythm models (e.g., from existing literature) relating light intensity input to the circadian phase output. When there is no circadian light stimulation, the model-free estimator is favoured and its output is used to calibrate the state of the model-based estimator. When the light input is present, the model-based estimator is used to speed up the model-free estimator. This combination of model-free and model-based estimators is new in the circadian rhythm field, and has shown significant improvement of circadian phase tracking fidelity under multiple light pulses. Using data generated from a well-accepted human circadian rhythm model, the convergence rate of the circadian phase estimation was observed increasing by a factor of two.

3. Light-based circadian rhythm model construction. By using the circadian phase estimate and the corresponding circadian light input, a model construction strategy has been developed to capture the input/output relationship (which allows prediction of circadian phase changes under different future lighting conditions). The methodology is based on a linear parameter varying (LPV) system formulation, with light intensity as the input and circadian phase as the output. This is a significant advance from the current state of the art of using either an analytical model, which only holds for averaged subjects, or the phase response curve, which does not capture the transient response. Since the model is constructed based on the measured biomarker signals, the model is "personalized" and could be adaptively updated based on measurements (for instance, as a person's circadian rhythm varies due to environment or physiological change, e.g., aging or disease).

4. Light-based circadian rhythm regulation. The model constructed above may be combined with the circadian rhythm estimate to automatically adjust the light input to the subject to optimally adjust the subject's circadian rhythm to fit the need (e.g., entrainment to a fixed schedule, shift to a new schedule, etc.). Compared with existing methods for light-based circadian rhythm entrainment, the approach disclosed herein is adaptive, based on estimated circadian phase and light input, thus matching to the characteristics of each individual subject.

Referring to the figures, FIG. 1 illustrates one embodiment of a system for facilitating real-time, model-less-based estimating of circadian phase of a subject (or biological system) 101, in accordance with one or more aspects of the present invention. As shown, system 100 includes a data processing system 111, configured with an adaptive circadian rhythm estimator 112, such as disclosed herein, and in communication with one or more sensing devices 114 and/or one or more input devices 116. One or more communication paths 113 may exist between data processing system 111 and sensing device(s) 114, and one or more communication paths 115 may exist between input device(s) 116 and data processing system 111.

One non-limiting example of a communications path may comprise one or more digital or analog connections operating via wired or wireless technology to facilitate communication between devices. For instance, a communications path may include a wired connection, an optical connection, and/or a wireless connection. Examples of wireless connections include, but are not limited to, RF connections using a wireless protocol such as an 802.11x protocol, or the Bluetooth® protocol.

Data processing system 111 may include one or more digital or analog components such as data processing units which include one or more processors for performing one or more aspects of the invention described herein. Examples of data processing units which may be used in connection with one or more aspects of the present invention include personal computers (PCs), laptops, workstations, servers, computing terminals, tablet computers, microprocessors, application specific integrated circuits (ASIC), digital components, analog components, or any combination or plurality thereof. Additional examples include mobile devices, for instance personal digital assistants (PDAs) or cellular devices such as smart phones. Additionally, a data processing unit may comprise a stand-alone unit, or a distributed set of devices.

Data processing system 111 may additionally comprise one or more other types of components, such as one or more data storage devices or databases for data logging, storage, and/or retrieval. At least some of the components of data processing system 111 itself may be interconnected by one or more communications paths, such as described above.

As illustrated, data processing system 111, with adaptive circadian rhythm estimator 112, may be in communication with a display or store device 118 for, for instance, for facilitating subsequent circadian rhythm modeling using the estimated circadian phase and/or for facilitating subsequent circadian rhythm regulation, as explained further herein.

Sensing device(s) 114 of FIG. 1 may be provided for obtaining measured biological data, for instance, a masked biological or physiological signal for the subject undergoing analysis, and as noted, may be in communication with one or more components of data processing system 111. As one specific example, sensing device(s) 114 may be in communication with a data storage device or buffer of data processing system 111, and sense biological data of a subject for processing in real-time by data processing system 111.

The one or more input devices 116 may be provided to facilitate input to and interaction with data processing system 111. Input devices may themselves comprise one or more data processing units, such as a data processing unit as described above. In one embodiment, input device(s) 116 may be provided as one or more components of data processing system 111 itself, or may be provided separate from data processing system 111 and in communication with one or more components thereof (such as depicted in FIG. 1). In one example, input device(s) 116 may facilitate inputting one or more circadian pacemaker goals for a subject for use in circadian rhythm regulation, as described herein.

Figure 2A:
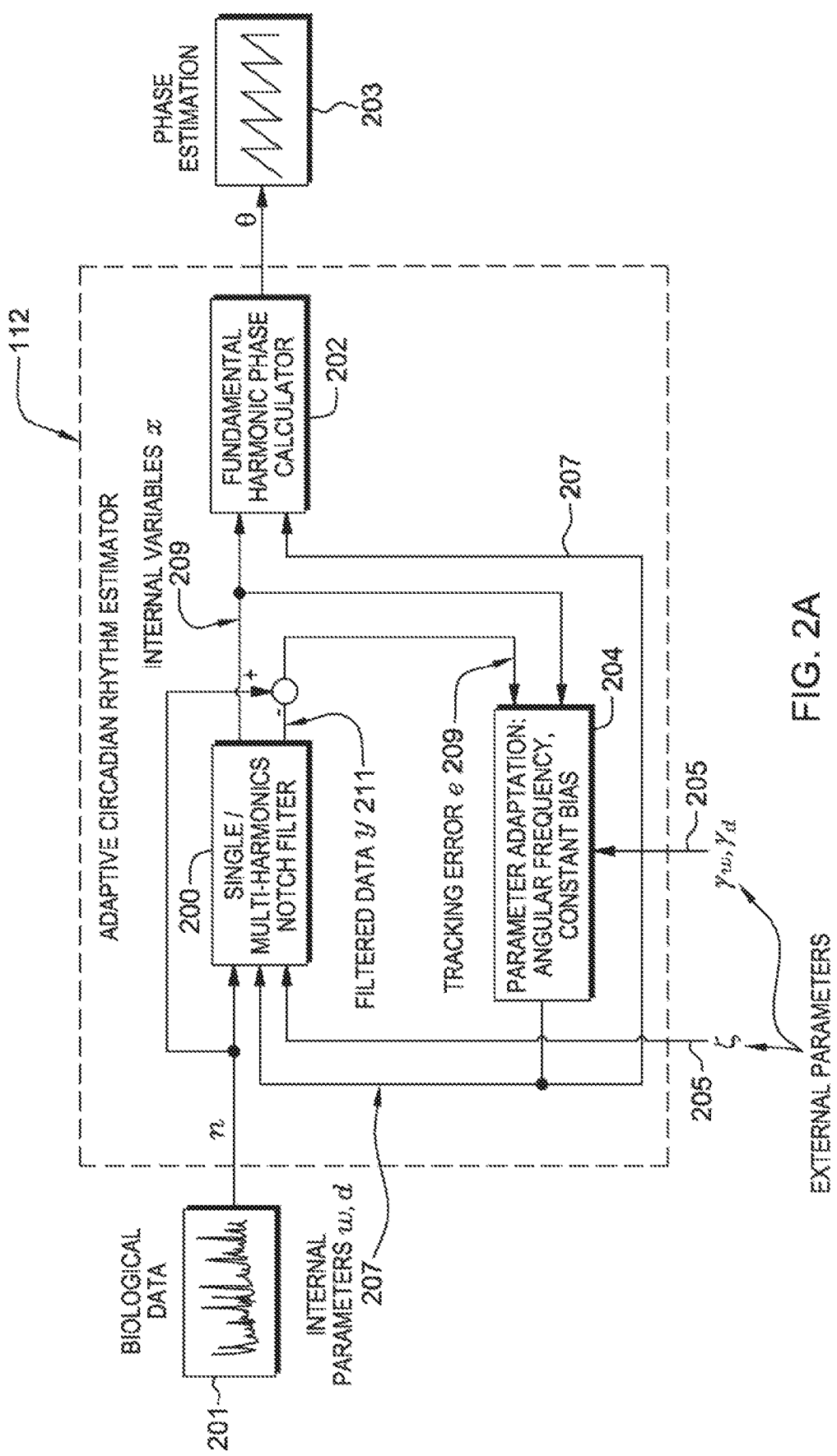
FIG. 2A depicts one embodiment of the adaptive circadian rhythm estimator of the system of FIG. 1, which provides an adaptive circadian phase estimate for a subject from a sensed biological signal obtained from the subject, in accordance with one or more aspects of the present invention.

FIG. 2A depicts one embodiment of an adaptive circadian phase estimator 112, in accordance with one or more aspects of the present invention. By way of example, the adaptive circadian rhythm estimator 112 may be programmed into a data processing system such as described above in connection with FIG. 1. Biological or physiological data n 201 is obtained, which can serve as circadian markers, such as activity level, core body temperature, hormone concentration, etc. The biological data is sensed or measured at a certain sampling rate, and provided as a biological signal to the estimator 112 in real-time (in one embodiment). Adaptive frequency tracking 200 is employed by the adaptive circadian rhythm estimator 112. In the example illustrated in FIG. 2A, this adaptive frequency tracking utilizes single-harmonic or multi-harmonic filtering, and in one approach, uses an adaptive notch filter.

The sensed biological signal is processed by the adaptive frequency tracking 200 (for instance, notch filter). An example of a notch filter with two harmonics is set out in Equations (1) below:

$$\begin{aligned} \dot{x}_1 &= x_2 \\ \dot{x}_2 &= \omega^2\left(n - d - \frac{2\zeta x_4}{2\omega}\right) - 2\zeta\omega x_2 - \omega^2 x_1 \\ \dot{x}_3 &= x_4 \\ \dot{x}_4 &= (2\omega)^2\left(n - d - \frac{2\zeta x_2}{\omega}\right) - 4\zeta\omega x_4 - (2\omega)^2 x_3 \end{aligned} \quad (1)$$

Where the input/output, internal variables, internal parameters, and external parameters, are respectively defined below in Tables 1-4.

TABLE 1

| Input/Output | Description | Value at each time step |
|---|---|---|
| n | Input, measured circadian signal | Data from biological sensors |
| θ | Output, circadian phase estimate | |
| y | Auxiliary variable, filtered circadian, signal | |
| e | Auxiliary variable, tracking error | |

TABLE 2

| Internal variables | Description | Value at initialization |
|---|---|---|
| $x_1$ | State variable for $1^{st}$ order oscillator | 0 |
| $x_2$ | State variable for $1^{st}$ order oscillator | 0 |
| $x_3$ | State variable for $2^{nd}$ order oscillator | 0 |
| $x_4$ | State variable for $2^{nd}$ order oscillator | 0 |

TABLE 3

| Internal parameters | Description | Value at initialization |
|---|---|---|
| d | Constant bias of the biological signal | Typical values † |
| ω | Angular frequency of circadian rhythm | 2π/24 (rad/h) |

† Initial values set for typical average values for the biological data used.

TABLE 4

| External parameters | Description | Typical value |
|---|---|---|
| ζ | Notch width of the filter | 0.3* |
| $Y_d$ | Adaptation rate of constant bias | 0.001‡ |
| $Y_\omega$ | Adaptation rate of angular frequency | 0.0001‡ |

*Typical value shown. To be manually tuned to balance between filter output convergence and noise sensitivity.
‡Typical values shown. To be manually tuned to balance between parameter adaptation convergence rate and noise sensitivity.

The notch filter is defined by several parameters, including: a notch width determined by a constant external parameter (ζ) 205, listed in Table 4; an angular frequency of the notch determined by an adjustable internal parameter (ω) 207, listed in Table 3; and the constant bias of the biological data (ω) and an adjustable internal parameter (d) 207, listed in Table 3. The constant external parameter (ζ) may be tuned, in one example, manually, to balance the filter output convergence rate and the filter's sensitivity to noise.

The notch filter 200 produces two sets of outputs, the internal state (x) 209, listed in Table 2, and the filtered biological data (y) 211, listed in Table 1. The evolution of the internal state for the example two-harmonic notch filter is given by Equations (1) above, and the filter biological or physiological data (y) is given by Equations (2):

$$\begin{aligned} y &= d + \frac{2\zeta x_4}{2\omega} + \frac{2\zeta x_2}{\omega} \\ e &= n - y \end{aligned} \quad (2)$$

Where the difference between the measured biological data (n), and the filtered biological data (y), are referred to as a tracking error (e) 213, listed in Table 1.

The tracking error (e) 213 and the internal states of the notch filter (x) 209 are provided to an internal parameter adaptation facility or block 204, which updates the adjustable parameters (d) and (ω) 207, listed in Table 3, based on the size of the tracking error, (e) 213. An example of the update rules is shown in Equations 3 below:

$$\begin{aligned} \dot{\omega} &= -\gamma_\omega \omega^2 e x_1 \\ \dot{d} &= \gamma_d e \end{aligned} \quad (3)$$

The constant parameters ($\gamma_d$, $\gamma_\omega$) 205, listed in Table 4, in the update rule of Equations (3), determine the adaptation rate. The constant external parameters ($\gamma_d$, $\gamma_\omega$) are tuned manually, in one example, to balance between the parameter adaptation convergence rate and the sensitivity to noise.

As noted, the outputs of the parameter adaptation block 204 are the adjustable parameters (d) and (ω), which are used in the notch filter 200, hence the name "adaptive notch filter", as well as the circadian phase estimation block 202, which produces a circadian phase estimate using, for instance, the example Equation (4) below:

$$\theta = \tan^{-1}\left(-\frac{x_2}{x_1 \omega}\right) \quad (4)$$

Figure 2B:
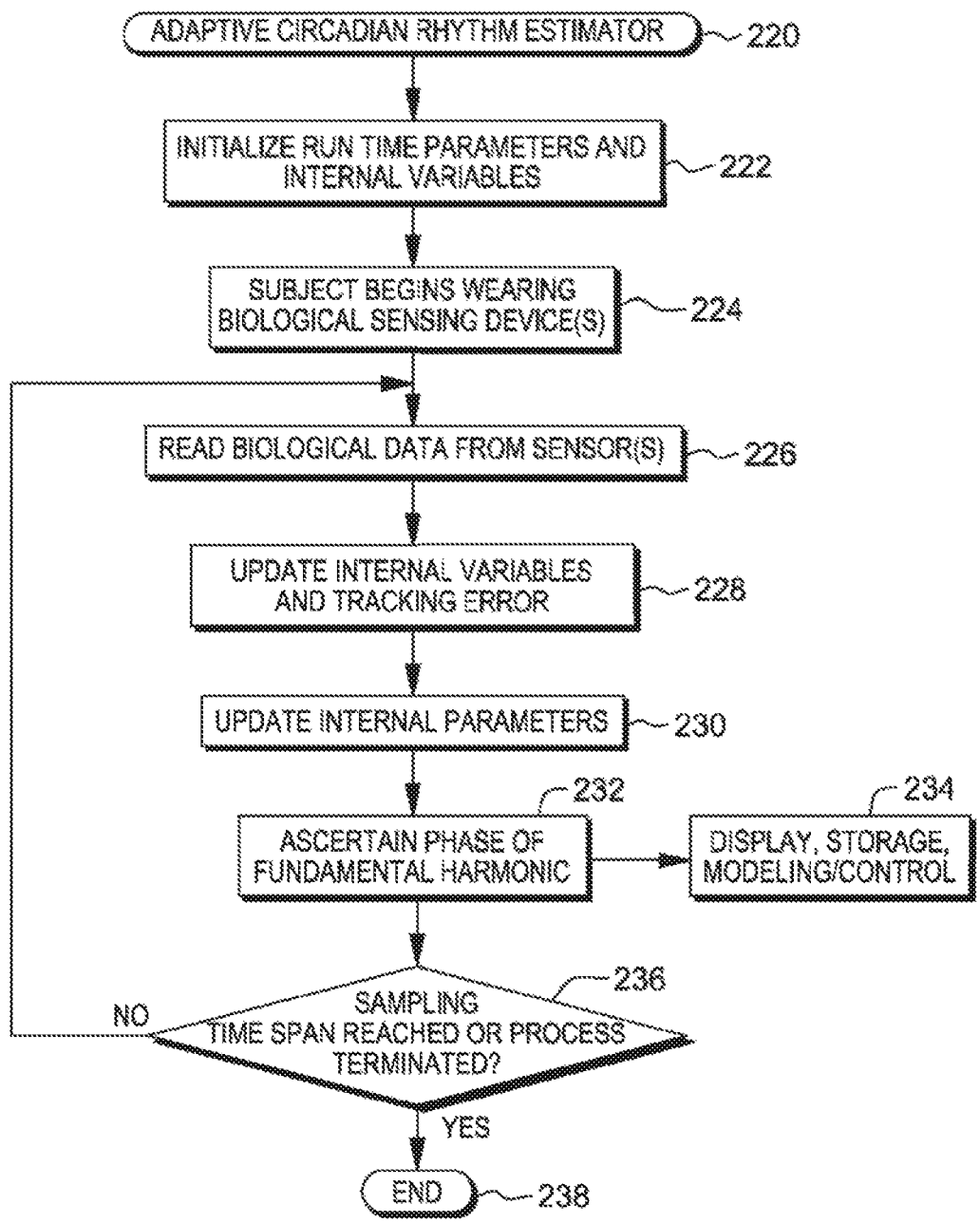
FIG. 2B depicts a process overview of one embodiment of adaptive circadian phase estimating, in accordance with one or more aspects of the present invention.

FIG. 2B illustrates one example of processing implemented by the circadian phase estimator 112 of FIG. 2A. Referring to FIG. 2B, adaptive circadian rhythm estimation 220 begins with initialization 222, including, for instance, initializing of the internal states x according to Table 2 above (which may be alternatively set to other values to speed up convergence), and initializing adjustable parameters d, ω, according to Table 3, and the constant parameters according to Table 4. In addition, the total running time is initialized according to an operator's input, or a default value (e.g., 1 or 2 weeks).

Data collection is commenced 224 with, for example, a subject beginning wearing a biological sensing device, for instance, in the case of a human, the subject begins wearing a device equipped with physiological data sensors, such as commercially available sensing devices, such as FitBit devices, manufactured by FitBit, Inc., of San Francisco, Calif., USA, and GT3X devices, manufactured by Actigraph, of Pensacola, Fla., USA, and other devices.

Biological data (n) is read from the sensors 226, which may be measured periodically, for instance, at one sample per minute. The sampling period may be denoted as Δt, and at timestep k, the measured biological data may comprise $n_k$.

Processing then updates 228 the internal variables 209 (see FIG. 2A), and the tracking error 213 (FIG. 2A). In addition, processing updates 230 the internal parameters 207 (see FIG. 2A). These updates 228, 230 may be performed as described below.

Begin with loading the internal state variables and the adjustable parameters of the previous time step from the memory, $x_{1,k-1}, x_{2,k-1}, x_{3,k-1}, x_{4,k-1}$, and $\omega_{k-1}, d_{k-1}$, and load the previous physiological data point $n_{k-1}$. Use any appropriate ordinary differential equation (ODE) solver to solve Equations (1) above and update the internal state variables. For example, by using a semi-implicit Euler method, the update law for the internal states, Equation (1), become:

$$x_{1,k} = x_{1,k-1} + x_{2,k-1}\Delta t$$

$$x_{2,k} =$$
$$x_{2,k-1} + \left(\omega_{k-1}^2\left(n_{k-1} - d_{k-1} - \frac{2\zeta x_{4,k-1}}{2\omega_{k-1}}\right) - 2\zeta\omega_{k-1}x_{2,k-1} - \omega_{k-1}^2 x_{1,k-1}\right)\Delta t$$

$$x_{3,k} = x_{3,k-1} + x_{4,k-1}\Delta t$$

$$x_{4,k} = x_{4,k-1} +$$
$$\left((2\omega_{k-1})^2\left(n_{k-1} - d_{k-1} - \frac{2\zeta x_{2,k-1}}{\omega_{k-1}}\right) - 4\zeta\omega_{k-1}x_{4,k-1} - (2\omega_{k-1})^2 x_{3,k-1}\right)\Delta t$$

The filtered data Equation (2) becomes:

$$y_k = d_{k-1} + \frac{2\zeta x_{4,k}}{2\omega_{k-1}} + \frac{2\zeta x_{2,k}}{\omega_{k-1}}$$

and the tracking error is $e_k = n_k - y_k$. The parameter update can be expressed as:

$$\omega_k = \omega_{k-1} - \gamma_\omega \omega_{k-1}^2 e_k x_{1,k} \Delta t$$

$$d_k = d_{k-1} + \gamma_d e_k \Delta t$$

The estimated phase of the fundamental harmonic may be ascertained 232 using Equation (4) above, with the result sent to display, storage, etc., for use, for instance, in subsequent circadian rhythm modeling and/or circadian rhythm regulation 234, as described further below. Unless the phase estimation is terminated, or the preset running time has been reached 236, processing loops back to obtain further biological data at the next sampling time. Otherwise, processing ends 238.

Figure 3A:
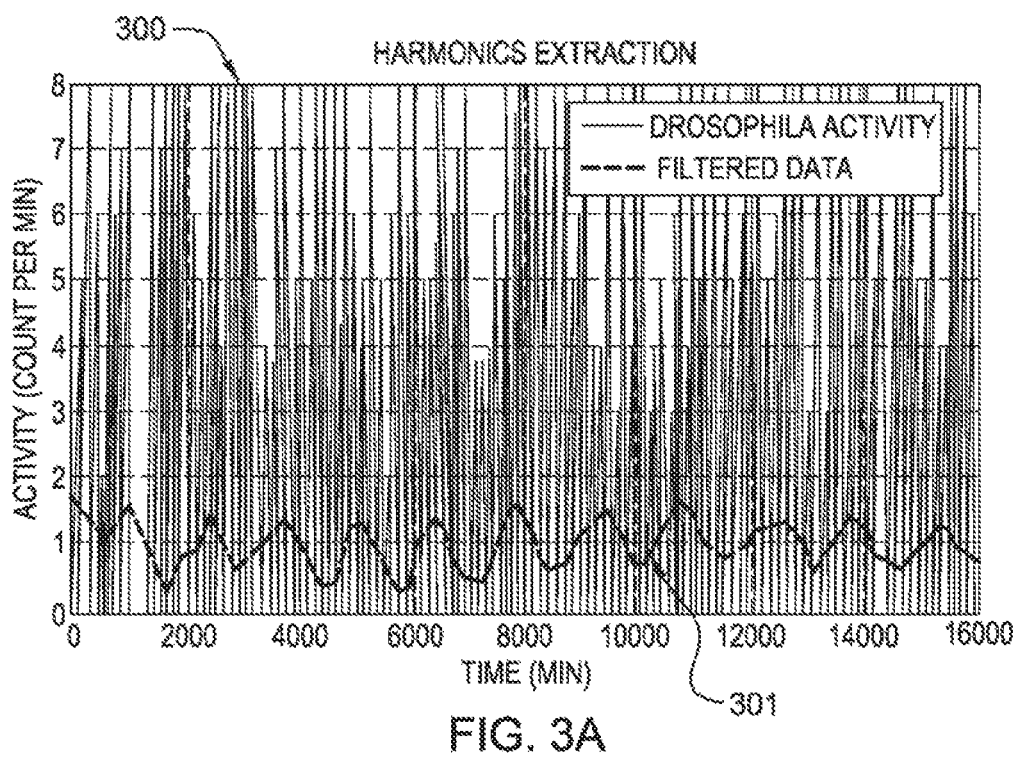
FIG. 3A is a graph of a sensed biological signal obtained from a *drosophila* subject, and which is to be adaptively filtered to ascertain circadian phase, in accordance with one or more aspects of the present invention.
Figure 3B:
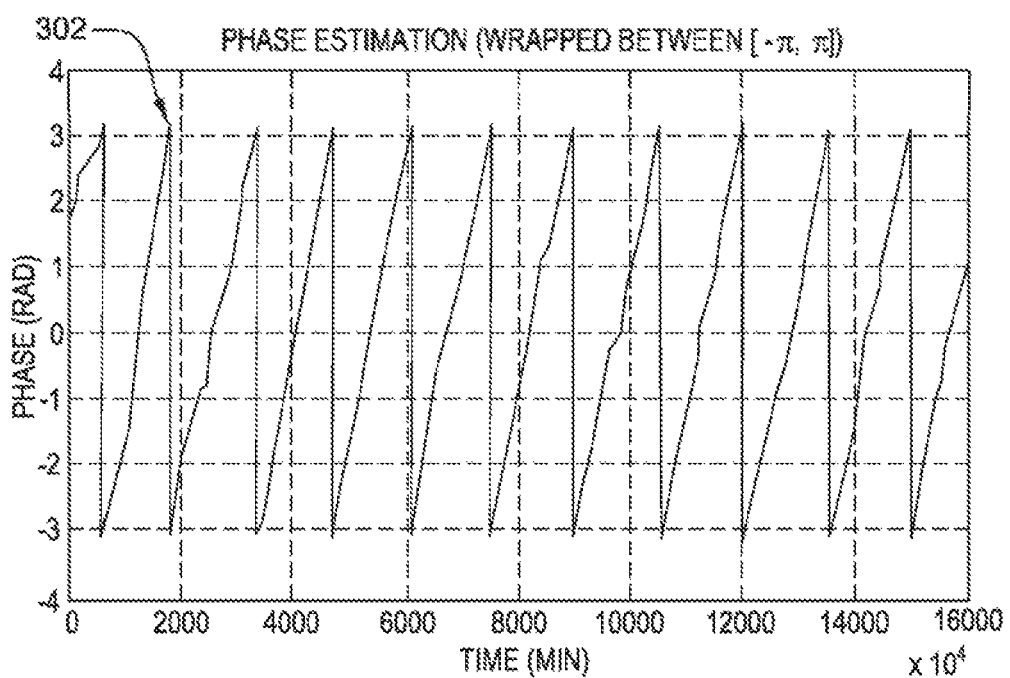
FIG. 3B is a graph of estimated circadian phase of the *drosophila* subject obtained using adaptive frequency tracking of the sensed biological signal of FIG. 3A, in accordance with one or more aspects of the present invention.

To demonstrate efficacy of the above-disclosed circadian phase estimator, *drosophila* locomotor activity data 300 (FIG. 3A) was obtained using *drosophila* activity monitoring (corresponding to the physiological data n). The *drosophila* is in complete darkness and its circadian system is free-running. In this example, the sampling rate is 1 sample per minute. By applying the circadian phase estimator with two harmonics, the noisy activity data is filtered 301 (corresponding to the filtered physiological data y), discussed above, and the circadian phase (302) (Θ) is extracted continuously, as displayed in FIG. 3B.

Figure 4A:
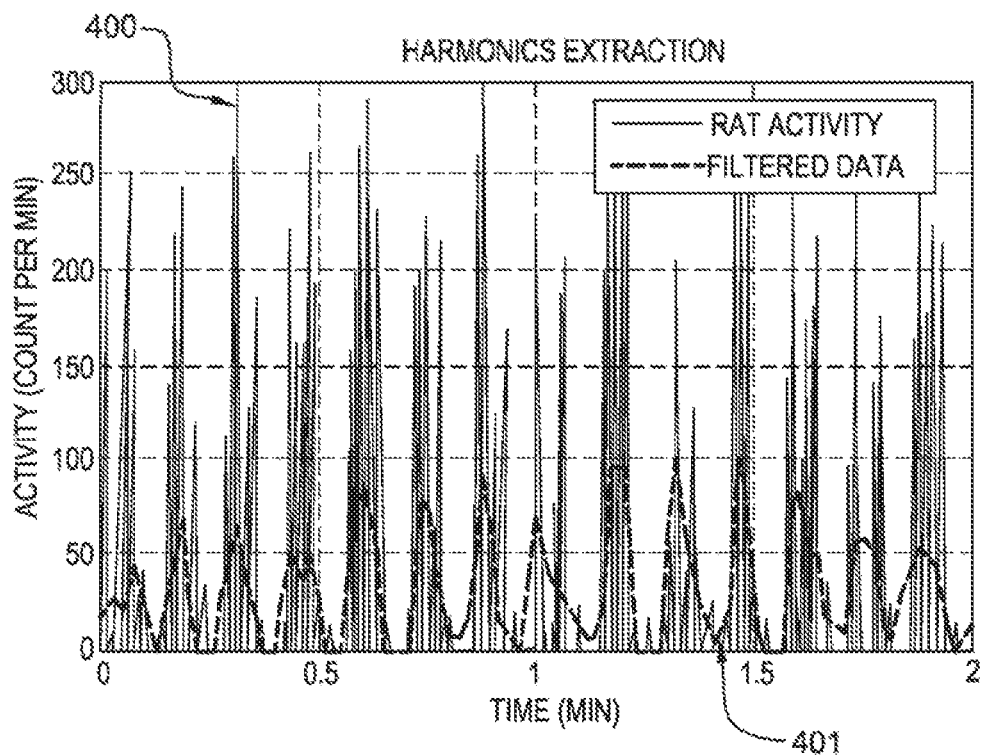
FIG. 4A is another example of a sensed biological signal obtained from a rat subject, and which is to be adaptively filtered to ascertain circadian phase, in accordance with one or more aspects of the present invention.
Figure 4B:
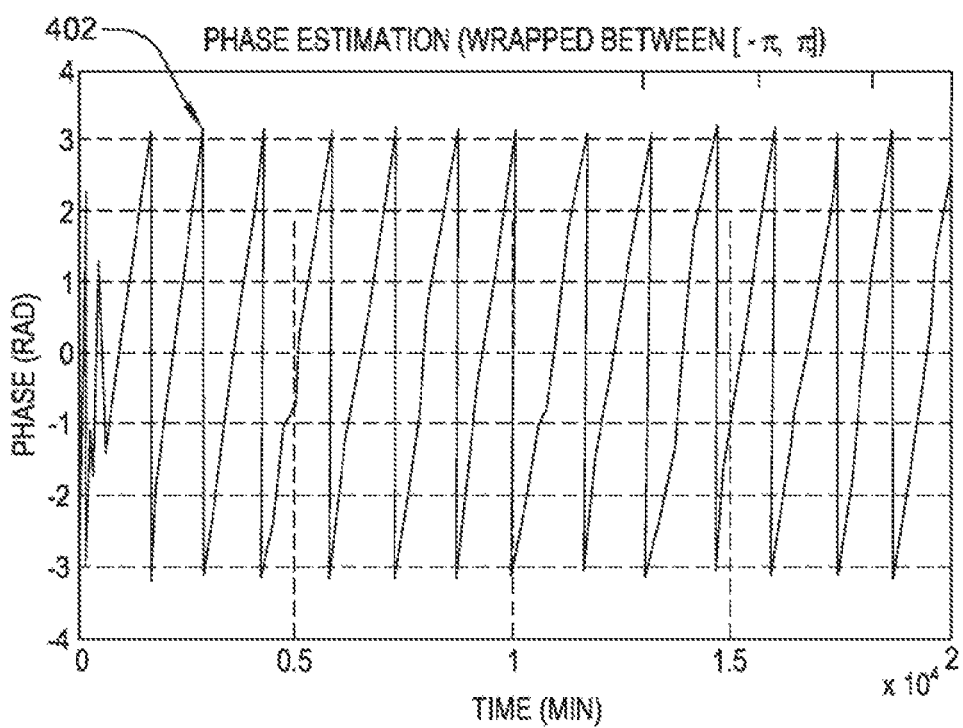
FIG. 4B is a graph of estimated circadian phase of the subject obtained using adaptive frequency tracking of the sensed biological signal of FIG. 4A, in accordance with one or more aspects of the present invention.

As another demonstration of efficacy, the above-disclosed circadian phase estimator was applied to rat locomotor activity level 400 (FIG. 4A) collected from rotation of wheel-cages (and corresponding to the physiological data n). The sampling rate was one sample per ten minutes. By applying the circadian phase estimator with two harmonics, the filtered data 401 (corresponding to the filtered physiological data y) and the circadian phase 402 (FIG. 4B) may be extracted continuously.

The above-discussed circadian phase estimator (using, for instance, adaptive notch filtering) uses only sensed or temporally past biological data to estimate in real-time the circadian phase of a subject. When light stimuli are introduced to produce additional circadian phase shift, the adaptive notch filter approach does not directly take the light input into account, resulting in a delay in convergence of the estimated circadian phase to the actual circadian phase. To accelerate convergence of the circadian phase estimate after a phase shift, the adaptive notch filter based estimator may be combined with the prediction capability of a circadian phase model (as explained below in connection with FIGS. 5A-6). In particular, a circadian phase model may be obtained from circadian oscillation models such as the Kronauer human circadian model, or biochemical oscillator model. Such model can predict the circadian phase shift due to light or other input stimuli, but are only an averaged model for a given species and cannot capture individual variations. However, the circadian phase model may be combined with an adaptive notch filter such as described above to accelerate the convergence of the circadian phase estimate when there is an input-induced phase shift, such as a light-induced phase shift.

Thus, in this aspect of the invention, accelerating estimator convergence includes combining an adaptive filter based phase estimator and a circadian phase model based estimator for biasing one or the other based on the presence of light or other input that causes circadian phase shifts:

1) In complete darkness or entrainment to a periodic stimulus, the phase estimate is based, for instance, on the adaptive notch filter, and the circadian phase model is regulated to track the circadian phase estimate of the adaptive notch filter.
2) In the case of a phase-shifting stimulus (e.g., light stimulus), the circadian model makes phase shift prediction, using the adaptive notch filter circadian phase estimate just before the stimulus as the initial condition, and the stimulus measurement as input. In this mode, the internal state of the adaptive filter is adjusted to follow the phase prediction of the circadian model.

Figure 5A:
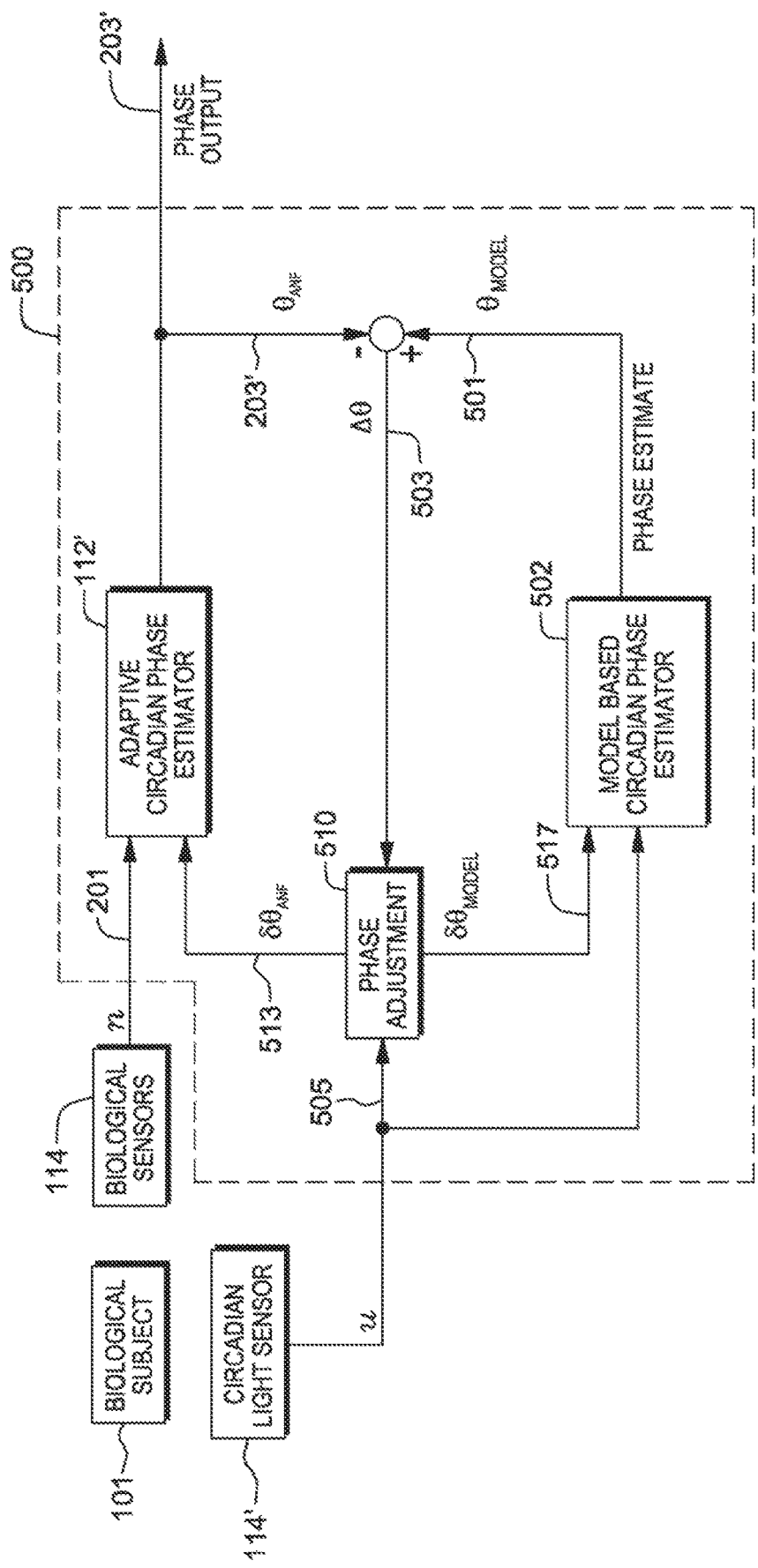
FIG. 5A illustrates one embodiment of an accelerated adaptive circadian phase estimator with a feedback loop for accelerating estimation of circadian phase from the sensed biological signal using adaptive frequency tracking, in accordance with one or more aspects of the present invention.

By way of example, referring to FIG. 5A, biological or physiological data n can serve as a circadian marker, such as activity level, core body temperature or hormone concentration obtained from a subject 101 using biological sensors 114. The data is processed by the adaptive circadian phase estimator 112 and a circadian phase estimate 203' is provided in real-time.

A circadian light sensor 114' measures the circadian light reception at the subject's eye level. As used herein, a circadian light measurement ascertains intensity of the portion of the light spectrum that stimulates the biological circadian system. Commonly used light sensors may be equipped with appropriate filters to only measure the circadian light intensity (examples of this method are a daysimeter and dimesimeter developed at the Lighting Research Center at Rensselaer Polytechnic Institute, Troy, N.Y.).

The measured circadian light data is provided to a circadian phase model 502, which predicts the circadian phase 501.

The difference between the estimated circadian phases 203', 501 of the adaptive circadian phase estimator 112 and model based circadian phase estimator 502, together with the circadian light input information 505, is used by the phase adjustment facility or block 510, which includes a tunable gain element to generate phase corrections for the two circadian phase estimators, in order to minimize their phase difference.

The phase adjustment facility 510 weighs the relative credibility between the phase estimates from the adaptive circadian phase estimator 112 and model phase estimator 502 based, for instance, on the following:

During free-running, the estimate of the adaptive circadian estimator is more reliable. The phase correction 513 for the adaptive circadian estimator is small and phase correction 517 for the model phase estimator provides the feedback to steer the model phase estimate 501 towards the adaptive circadian phase estimate 203'.

With light stimulus, the situation is reversed. Since the circadian model 502 responds to the light stimulus faster, when a light stimulus is detected, the phase correction 517 for the model 502 is small while the phase correction 513 for the adaptive circadian estimator 112 provides the feedback to steer the adaptive circadian estimator 112 more quickly towards the model circadian phase estimate 501.

To illustrate this phase estimate acceleration, consider the following embodiment of adaptive phase estimator 112, model based phase estimator 502, and the phase adjustment block 510. For simplicity, the adaptive phase estimator 112 in this embodiment has only 1 harmonic. The adaptive phase estimator rule of Equations (5) now includes the additional phase correction $\delta\Theta_{ANF}$ 513:

$$\left.\begin{array}{l}\dot{x}_1 = x_2 + 0.6x_2\delta\theta_{ANF} \\ \dot{x}_2 = \omega^2 n - \omega^2 x_1 - 2\zeta\omega x_2 - \omega^2 d - 0.6\omega^2 x_1\delta\theta_{ANF} \\ \dot{\omega} = \gamma_\omega \omega^2 x_1\left(n - d - \frac{2\zeta x_2}{\omega}\right) \\ \dot{d} = \gamma_d\left(n - d - \frac{2\zeta x_2}{\omega}\right)\end{array}\right\} \quad (5)$$

The description of the variables and the parameters are the same as Tables 1-4. The phase estimate 203' is given by:

$$\theta_{ANF} = \tan^{-1}\left(-\frac{x_2}{x_1\omega}\right).$$

The circadian phase model 502 is obtained from any oscillator model for circadian rhythm (examples include Kronauer's human circadian model, fruit fly biochemical model, etc.) by using, for example, procedures in E. Brown et al., "One the Phase Reduction and Response Dynamics of Neural Oscillator Populations", Neural Comput., Volume 16, No. 4, pages 673-714, 2004. One embodiment of the resulting circadian phase model, including the phase correction $\delta\theta_{model}$ 517, is given by Equation (6) below:

$$\dot{\theta}_{model} = \omega_0 + f_{model}(\theta_{model})u - 0.6\delta\theta_{model} \quad (6)$$

where $\theta_{model}$ 501 is the first based phase estimate $\omega_0$ is the free running angular frequency (for human, it is set at $$\omega_0 = \frac{2\pi}{24.2}$$

rad/hr), u is the circadian light stimulus, and $f_{model}(\theta_{model})$ characterizes the phase shift due to circadian light pulse input. A typical shape of this function is plotted in FIG. 5D, by way of example only.

The phase estimate discrepancy ($\Delta\Theta$) 503 is expressed by Equation (7) below:

$$\Delta\theta = \theta_{model} - \theta_{ANF} \quad (7)$$

Figure 5B:
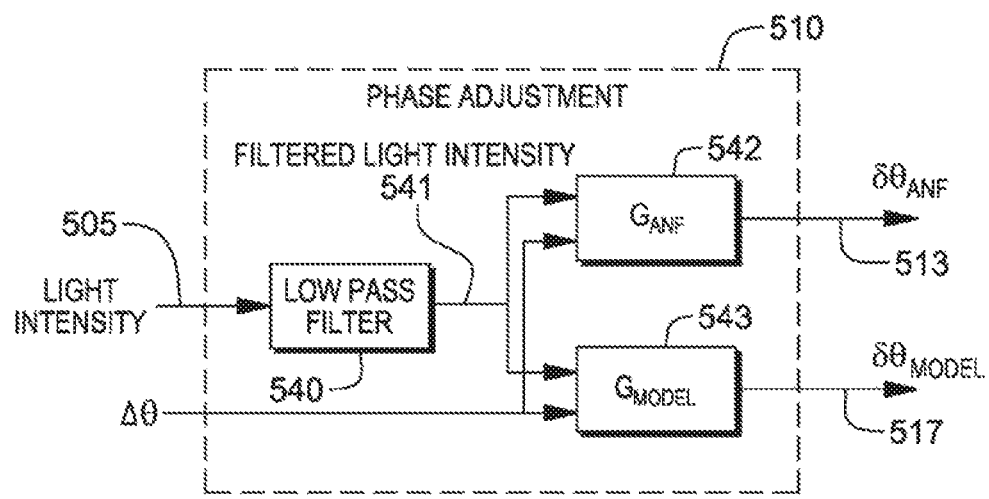
FIG. 5B depicts a block diagram of the tunable gain element of the accelerated adaptive circadian phase estimator of FIG. 5A, in accordance with one or more aspects of the present invention.

Referring to FIG. 5B, the phase adjustment block 510 generates phase corrections $\delta\Theta_{ANF}$ 513 and $\delta\theta_{model}$ 517 based on the circadian lighting conditions. One embodiment is given by a feedback with the variable gains of Equations (8):

$$\left.\begin{array}{l}\delta\theta_{model} = GAIN_{model}\Delta\theta \\ \delta\theta_{ANF} = GAIN_{ANF}\Delta\theta\end{array}\right\} \quad (8)$$

where $GAIN_{model}$ and $GAIN_{ANF}$ are gains that depend on the input circadian light. An example of these gains is given by Equations (9) below:

$$\left.\begin{array}{l}GAIN_{model} = \frac{1}{y+1} \\ GAIN_{ANF} = \frac{y}{y+1} \\ y = H(s)u\end{array}\right\} \quad (9)$$

where H(s) 540 is a low-pass filter such as one with the transfer function $H(s)=10^4/(s+0.1)$, with the circadian light (u) 505 as the input and (y) 541 as the output.

Figure 5C:
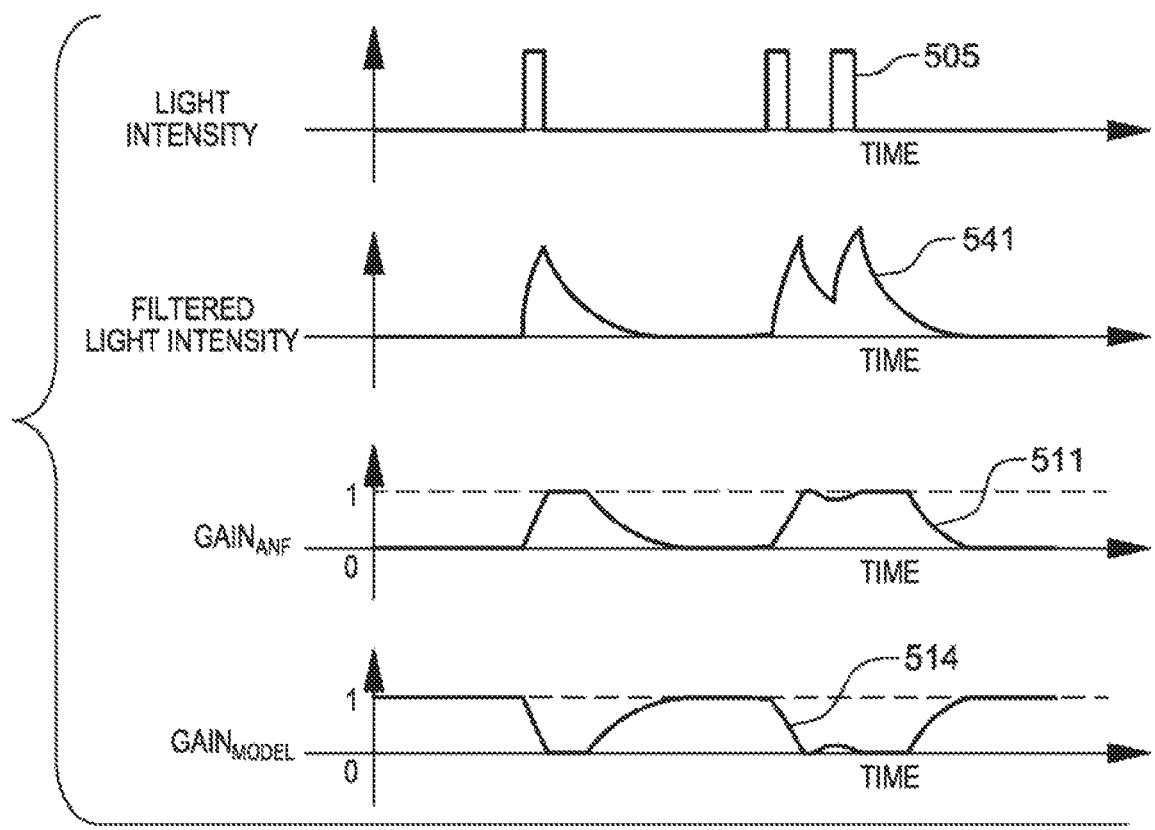
FIG. 5C provides example gain signal outputs for use in ascertaining phase corrections for the adaptive frequency tracking and the circadian phase model of the accelerated adaptive circadian phase estimator of FIG. 5A, in accordance with one or more aspects of the present invention.
Figure 5D:
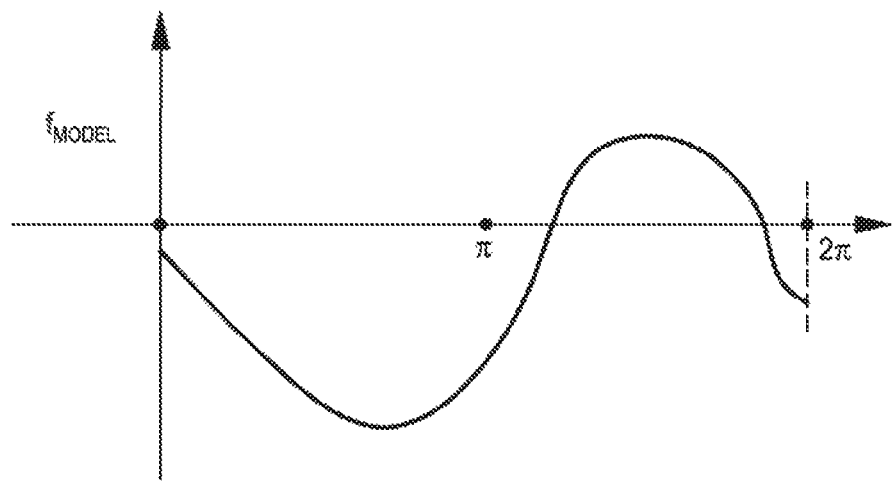
FIG. 5D is an example of an f_MODEL signal employed in one embodiment of adaptive frequency tracking, in accordance with one or more aspects of the present invention.

FIG. 5C demonstrates how the gains are adjusted according to light intensity. The light pulses 505 are filtered by the low-pass filter, and the filtered light intensity 541 is further processed by blocks 542 and 543, according to Equations (9) to produce the phase corrections. When in darkness, $GAIN_{model}$ 511 is low and $GAIN_{ANF}$ 514 is at the nominal value 1. In this case, the model based phase estimate converges towards the adaptive circadian phase estimator output. During and after light pulses, $GAIN_{ANF}$ rises to 1 and $GAIN_{model}$ drops to 0. In this case, the situation is reversed; the adaptive circadian phase estimator output now converges towards the model based phase estimate.

Figure 5E:
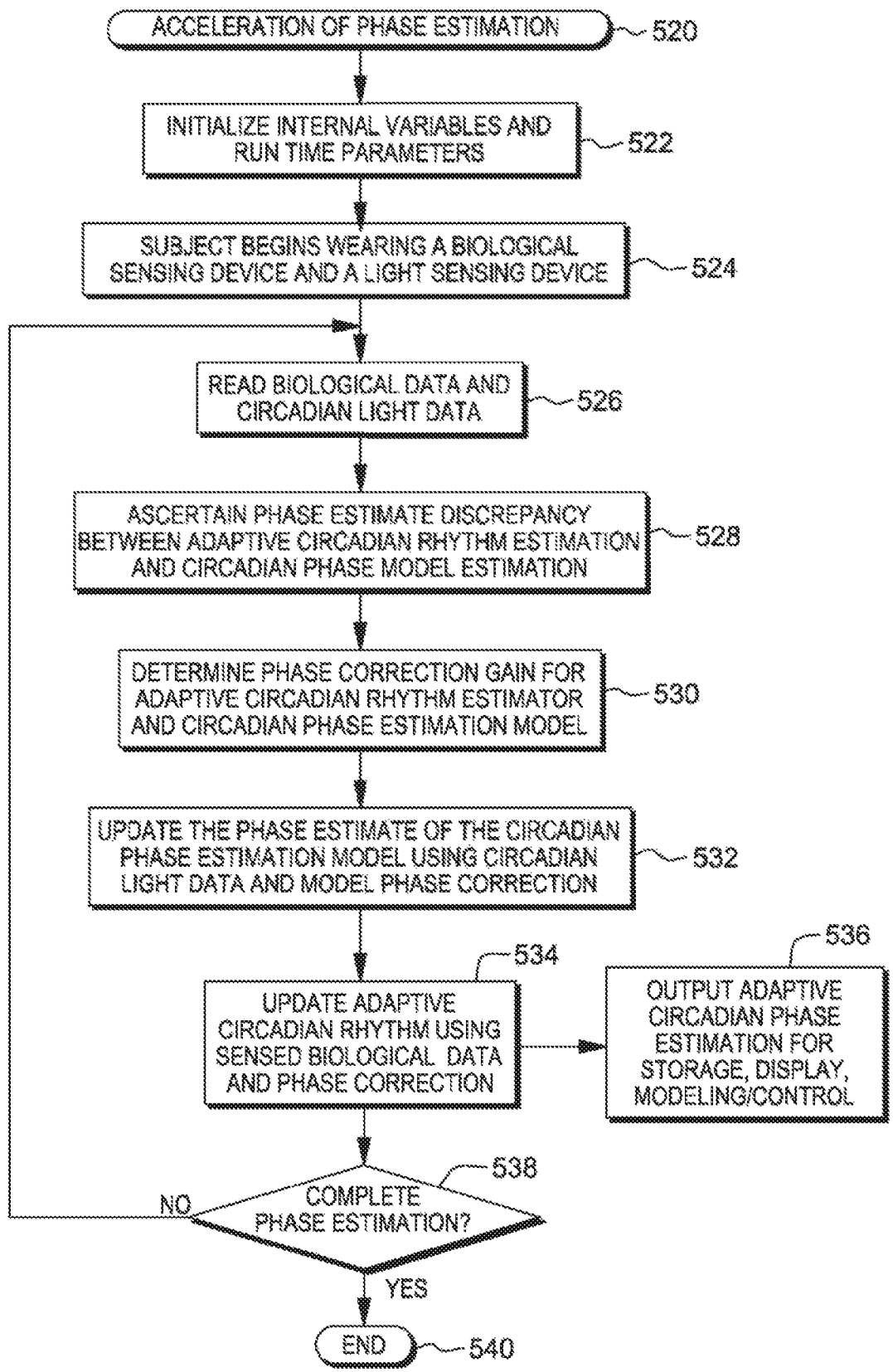
FIG. 5E is a process flow example for accelerating circadian phase estimation based on adaptive frequency tracking using, for instance, the accelerated adaptive circadian phase estimator of FIG. 5A, in accordance with one or more aspects of the present invention.

FIG. 5E illustrates an example of processing implemented by the accelerated circadian phase estimator of FIG. 5A. Referring to FIG. 5E, accelerated adaptive circadian rhythm estimation 520 begins with initialization 522 including, for instance, initializing of internal variables and runtime parameters 522. This may include initializing the internal state x according to Table 2 (or to other values, if desired, to speed up convergence), adjustable parameters d, ω according to Table 3, and the constant parameters according to Table 4, as well as initializing the total running time according to operator input or a default value (e.g., 2 weeks).

Processing begins data collection 524 using one or more devices. By way of specific example, a human subject may start wearing a device equipped with physiological data sensors (such as the above-reference, commercially available actigraph devices marketed as FitBit and GT3X). The physiological data and circadian light intensity are measured periodically, for example at one sample per minute, with the sampling period denoted as .DELTA.t. At time step k, the measured physiological data may be stored as $n_k$ and circadian light intensity as $I_k$.

Processing ascertains the difference between phase estimates 528 using the previous step estimation results $\Theta_{model,k-1}$ and $\Theta_{ANF,k-1}$ to compute $\Delta\Theta_{k-1}$ according to Equations (8) above.

The phase corrections are determined 530 using the light intensity data $I_k$ to update $\Theta_{model,k-1}$ according to Eq. (9), and the phase correction for ANF, $\delta\Theta_{ANF,k-1}$ by multiplying $\Delta\Theta_{k-1}$ with $GAIN_{ANF}$. The phase correction of the circadian model $\delta\Theta_{ANF,k-1}$ may be determined by multiplying $\Delta\Theta_{k-1}$ with $GAIN_{model}$ according to Eq. (8).

The output of the circadian phase model is updated 532 using the prior estimate $\theta_{model,k-1}$, the phase correction $\delta\Theta_{ANF,k}$ and the light intensity $I_k$ (by applying an appropriate ODE solver to Eq. (6) above.

Additionally, the adaptive circadian estimator updates its output 534 using the internal state variable and parameters at previous time step $x_{1,k-1}$, $x_{2,k-1}$, $\omega_{k-1}$, $d_{k-1}$, the phase correction $\delta\Theta_{ANF,k}$, and the physiological data $n_k$ by applying an appropriate ODE solver to Equation (4). The circadian phase estimate output ($\Theta_{ANF,k}$) may be provided, for instance, for storage, display or feedback control 536.

Unless an operator terminates the phase estimation processing or a pre-set running time has been reached 538, processing will return to read biological data and circadian light data 526 at the next sampling time. Otherwise, phase estimation processing is complete.

Figure 6:
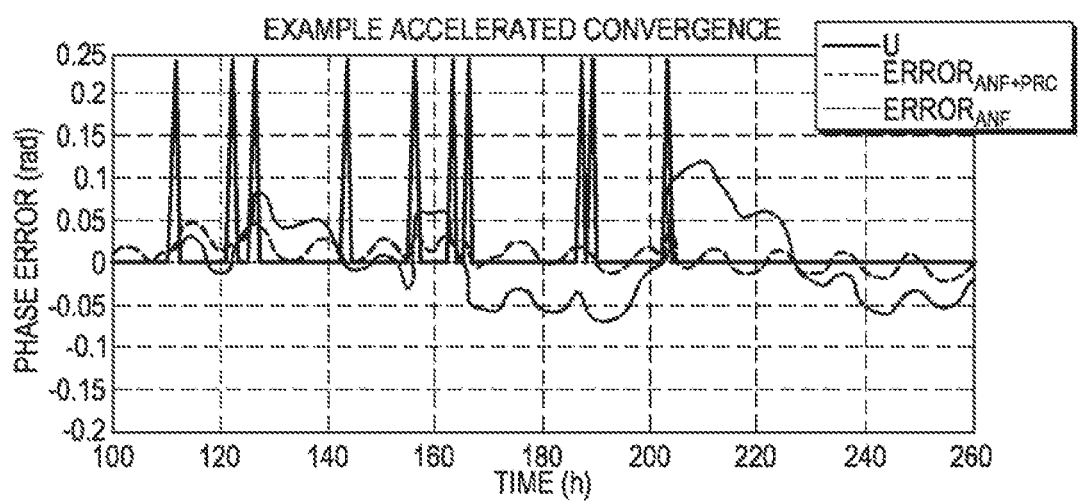
FIG. 6 illustrates acceleration of phase estimation by comparing the circadian phase estimation obtained using the adaptive circadian phase estimator of FIG. 2A, compared with the circadian phase estimation obtained using the accelerated adaptive circadian phase estimator of FIG. 5A, in accordance with one or more aspects of the present invention.

To demonstrate the efficacy of the circadian estimate acceleration, the Kronauer's human circadian model was used as an illustration. In this model, the measured physiological data is the output of the model (core body temperature). The parameters and the accelerated convergence estimator are the same as the example embodiment. In FIG. 6, light pulses are applied to a subject. Using the adaptive circadian estimator (FIG. 2A) alone, the phase estimation error converges to zero in about 24 hours 203, and using the accelerated convergence estimator (FIG. 5A), the phase estimation error 203' converges in much shorter time.

As noted above, an approach for ascertaining, or constructing, a light-based circadian rhythm model is also disclosed herein. By using a circadian phase estimate and the corresponding circadian light input, a model construction strategy is disclosed below to capture the input/output relationship, which in turn, allows prediction of circadian phase changes under different future lighting conditions. The method is based on using a linear parameter-varying (LPV) system formulation, with light intensity as the input and circadian phase as the output. Since the model is constructed based on measured biological signals, the model is "personalized" to the subject, and can be adaptively updated based on updated measurements.

In determining a light-based circadian rhythm model, a circadian phase model may play a role, but it is not tailored to individual circadian rhythms. A linear parameter-varying (LPV) model better approximates the circadian light input to circadian phase estimate output as a family of linear time-invariant (LTI) systems. An embodiment of this formulation is presented as Equations 10 below.

$$\begin{aligned} x_{k+1} &= A(\theta_k)x_k + B(\theta_k)u_k \\ \theta_k &= Cx_k + \theta_{k_{free\ running}} \end{aligned} \quad (10)$$

Where $x_k$ is the model state at time k, $\Theta_k$ is the estimated circadian phase, and $\Theta_{k\ free\ running}$ is the free running circadian phase when no circadian light is present. The circadian light input and estimated circadian phase output are measured and stored, and used to identify the matrices $A(\Theta_k)$, $B(\Theta_k)$, and C. In one embodiment, the observable canonical form is used, with C as a known constant matrix. Matrices A, B are functions of $\Theta_k$. Lighting and circadian phase estimation data may be used to identify matrices $A(\Theta_k)$, $B(\Theta_k)$, in the model for the best fit of Eqs. (10), with the measured data. In one embodiment, $A(\Theta_k)$ may vary little with $\Theta_k$. In that case, A may be replaced by a constant matrix.

Figure 7A:
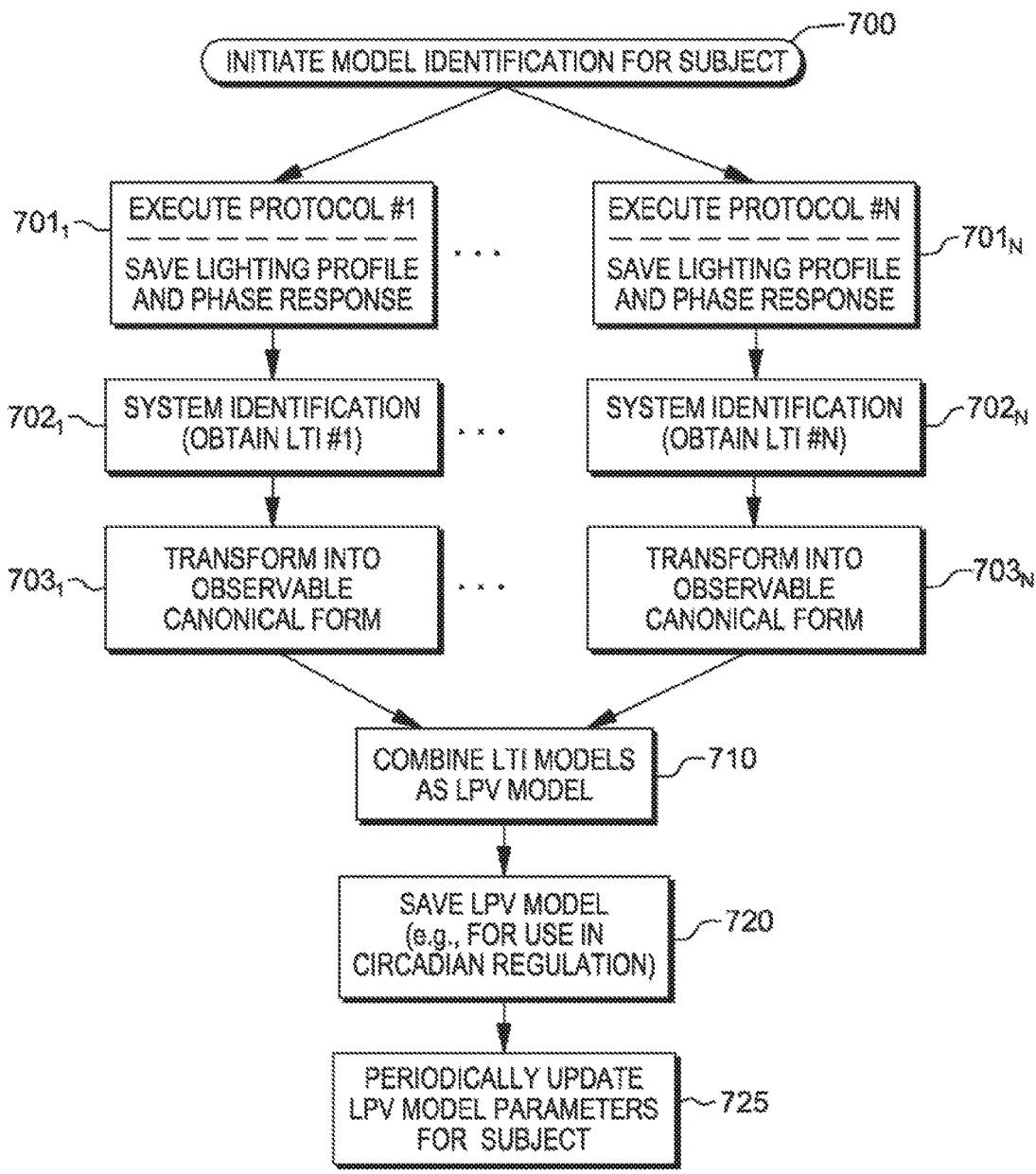
FIG. 7A illustrates one embodiment of a process for automatically ascertaining a light-based circadian rhythm model for a subject using a linear parameter-varying system formulation, in accordance with one or more aspects of the present invention.

In FIG. 7A, model identification is initiated 700 by, for instance, initializing data acquisition. In accordance with this process, N lighting protocols 701$_1$ ... 701$_N$ are separately applied, and both the circadian light input and circadian phase estimate output are obtained and saved. As an example, FIG. 7C depicts one lighting protocol which may be used in model identification. In this example, the variable N is set to 24, with each profile being for a different hour in a 24-hour period. As illustrated in FIG. 7C, for a period of time, for instance, a week, regular 12-hour light/dark cycles 740, 742, 744 are employed to entrain the subject's circadian rhythm. After entrainment, a short duration pulse 741, 743, 745, such as a 10-minute pulse, is applied at a specified time. In the example illustrated, the pulses 741, 743, 745 are spaced apart, about one hour, by way of example only. The identified $B(\Theta_k)$ from the processing of FIG. 7A will correspond to the timing of each pulse. To obtain circadian phase $\Theta$ in between pulses, any spline interpolation algorithm may be employed, such as the cubic spline, which ensures continuity and continuous slope at the interpolation points.

A standard systems identification algorithm is applied to the saved data to find the best linear time-invariant (LTI) model that fits with the obtained data for each lighting protocol $702_1 \ldots 702_N$. An example system identification approach which can be sued is the subsystems identification algorithm described in McKelvey et al., "Subspace-Based Multivariable System Identification from Frequency Response Data", IEEE Transaction on Automatic Control., Vol. 41, No. 7, pages 960-979, July 1996. The obtained LTI model is transformed to standard, observable canonical form $703_1 \ldots 703_N$. This procedure is repeated N times, with the lighting profile changed, such as described above in connection with FIG. 7C. The identified LTI models are then combined to form the linear parameter-varying (LPV) model expressed in Eq. (10), with interpolation (such as cubic spline interpolation) applied to the characterization of $B_k$ 710. The LPV model is saved for use in circadian regulation 720, and the LPV model parameters may be periodically updated for the individual subject 725.

Figure 7B:
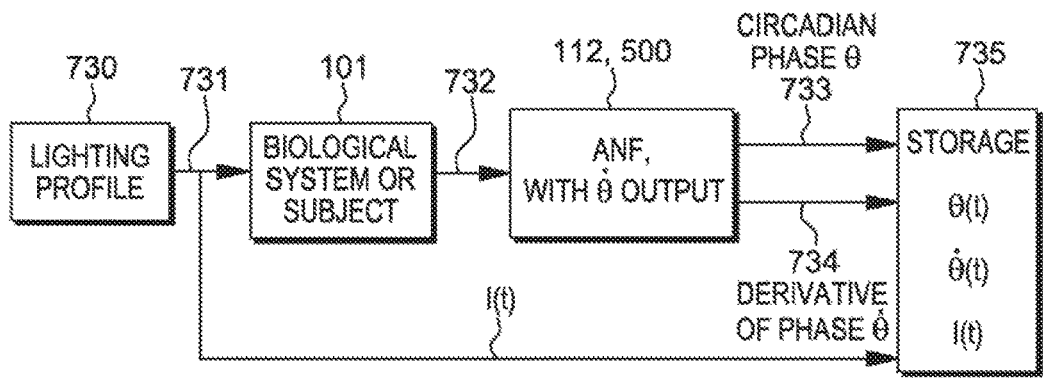
FIG. 7B is a block diagram of one embodiment of a process for linear time-invariant system identification, in accordance with one or more aspects of the present invention.

FIG. 7B depicts one example of protocol for LTI identification. A lighting profile, such as protocol 1 . . . N depicted in FIG. 7C, is applied as the circadian light intensity 731 to the biological system or subject 101. The circadian light intensity affects the circadian rhythm response of subject 101, and the biological signal output 732 is processed by the circadian phase estimator, for instance, estimator 112 (FIG. 2A), or estimator 500 (FIG. 5A), to generate the circadian phase (Θ), as well as its time derivative ( ). The lighting profile, (Θ, and time derivative) are then stored 735 for use in identification of the linear time-invariant system, as well as the linear parameter-varying model, as described above in connection with FIG. 7A.

FIG. 7D illustrates one example of the pulse response of the time derivative ( ) or subspace identification. In this figure, an example circadian phase output is illustrated when a lighting profile is applied which includes a series of entrainment pulses 750, and a short pulse 751 following the entrainment pulses. The circadian phase (Θ) shows entrainment during the entrainment phase 752, and a phase shift 753 when the short light pulse 751 is applied. The time derivative for the circadian phase is constant during the entrainment phase 754, and a circadian phase shift 755 is registered after the light pulse is applied.

FIGS. 8A-10B illustrate the efficacy of the resultant light-based circadian rhythm model constructed as described above in connection with FIGS. 7A-7D. The identified models in these examples are second-order systems.

Figure 8A:
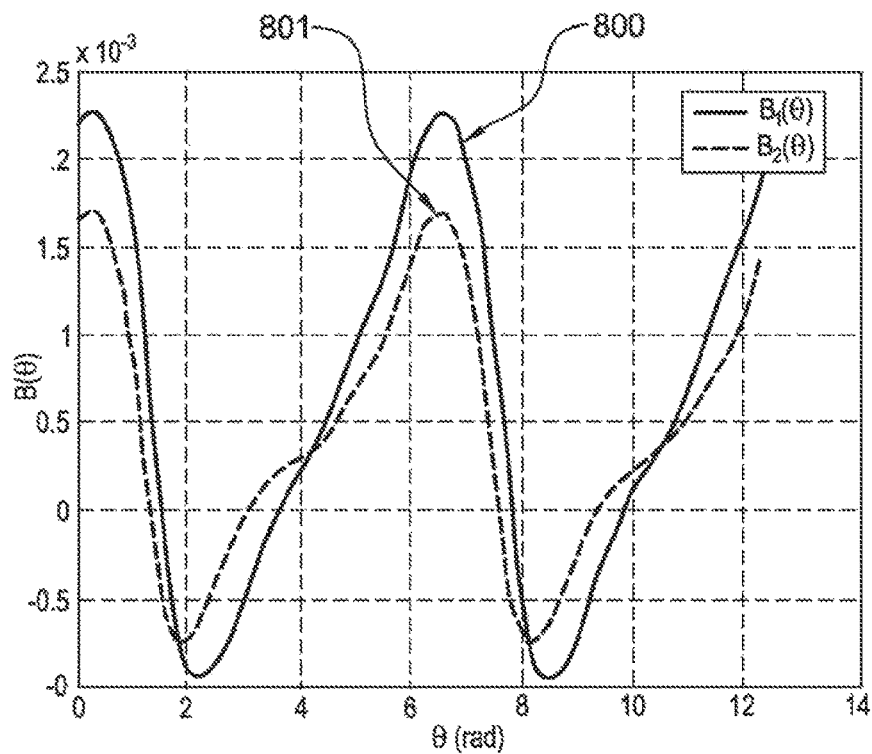
FIG. 8A illustrates the family of B(Θ) from a linear parameter-varying (LPV) model obtained using data generated from the widely accepted human circadian models developed by R. E. Kronauer et al., and obtained in accordance with one or more aspects of the present invention.
Figure 8B:
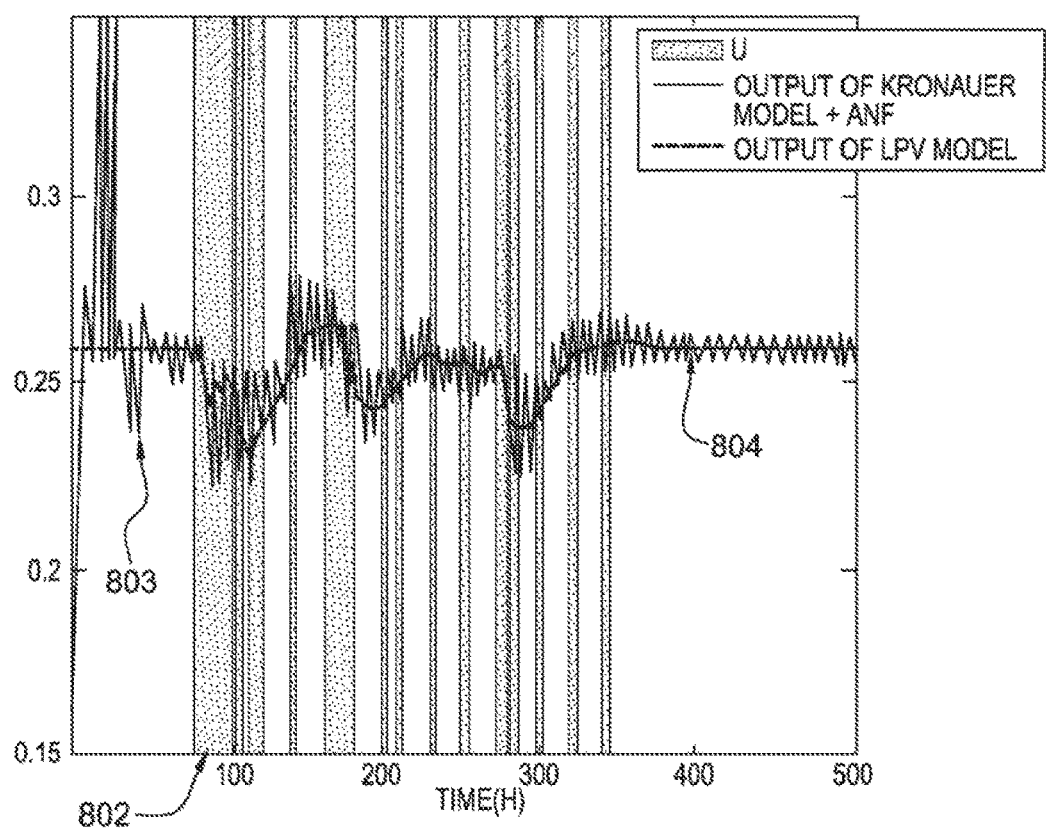
FIG. 8B illustrates the ability of the LPV model to predict the circadian phase response using the Kronauer circadian model for simulation, in accordance with one or more aspects of the present invention.

In FIGS. 8A & 8B, the output of the obtained LPV model is compared against the output of the human circadian rhythm model developed by R. E. Kronauer, and described in R. E. Kronauer, "A Quantative Model for the Effects of Light on the Amplitude and Phase of the Deep Circadian Pacemaker, Based on Human Data", Sleep '90, 10.sup.th European Congress on Sleep Research, page 306, Dusseldorf Ponteagel Press, 1990; R. E. Kronauer et al., "Quantifying Human Circadian Pacemaker Response to Brief Extended, and Repeated Light Stimuli Over the Phototopic Range" Journal of Biological Rythms, Volume 14, No. 6, pages 501-516, 1999; and M. E. Jewett et al., "Revised Limit Cycle Oscillator Model of Human Circadian Pacemaker", Journal of Biological Rhythms, Volume 14, No. 6, pages 493-499, 1999. For the Kornauer Model, the two components of the identified B(Θ) matrix are depicted in FIG. 8A as 800, 801. The comparison of the identified model output for a given circadian light input 802 shows using the adaptive circadian phase estimation alone 803 is noisier and lags behind the identified LPV model output 804.

Figure 9A:
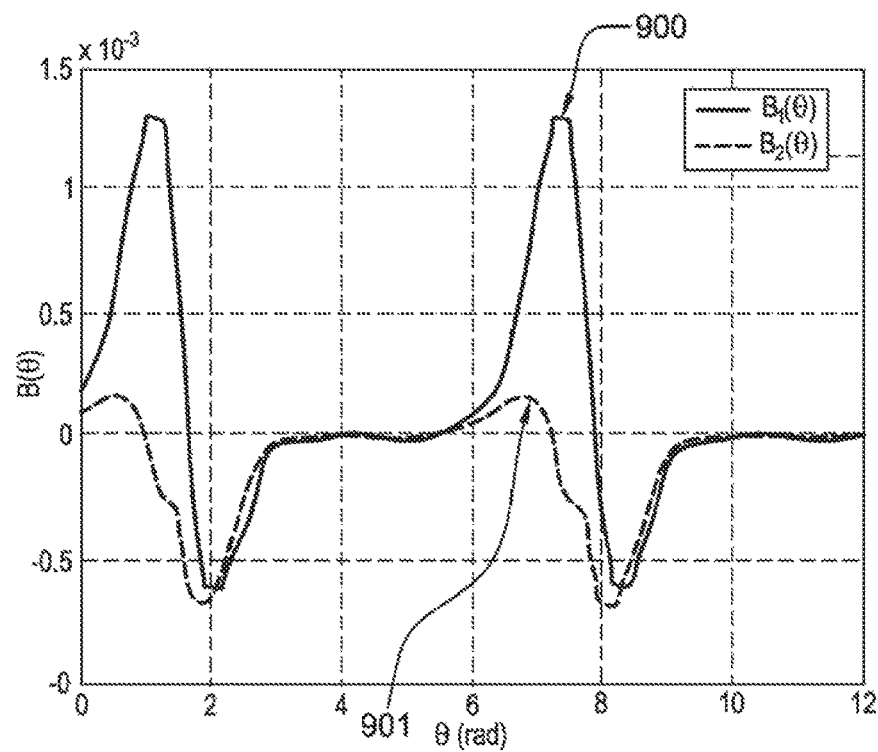
FIG. 9A illustrates the family of B(Θ) from an LPV model obtaining using data generated from the *Drosophila* circadian model, and obtained in accordance with one or more aspects of the present invention.
Figure 9B:
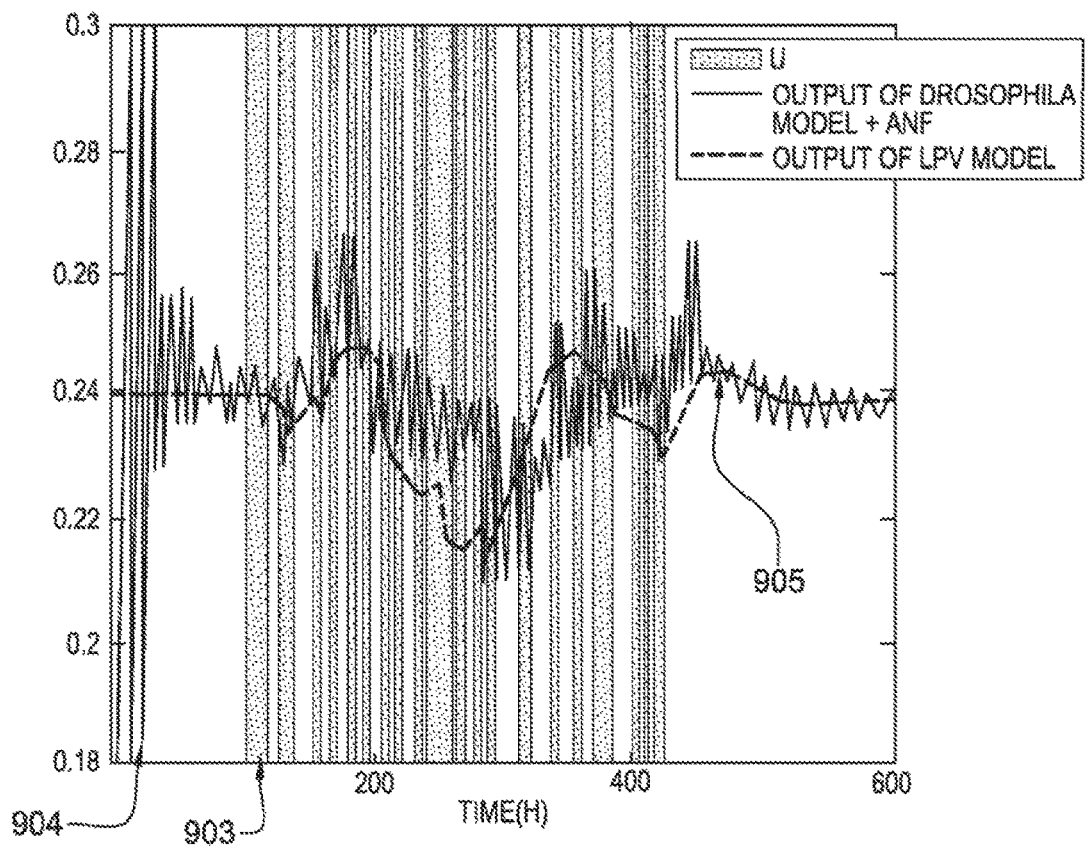
FIG. 9B illustrates the ability of the LPV model to predict the circadian phase response using the *Drosophila* circadian model for simulation, in accordance with one or more aspects of the present invention.

FIGS. 9A & 9B illustrate the identified result using the biomolecular circadian rhythm model for *drosophila* described in J. C. Leloup et al., "A Model for Circadian rhythms in *Drosophila* Incorporating the Formation of a Complex Between the PER and TIM Proteins", Journal of Biological Rhythms, Vol. 13, pages 70-87, 1998. For the *Drosophila* Model, the two components of the identified B(Θ) matrix are labeled 900, 901 in FIG. 9A, and the comparison of the identified model output for a given circadian light input 903 shows the noisy adaptive circadian phase estimator 904 result, compared with the identified model output 905.

Figure 10A:
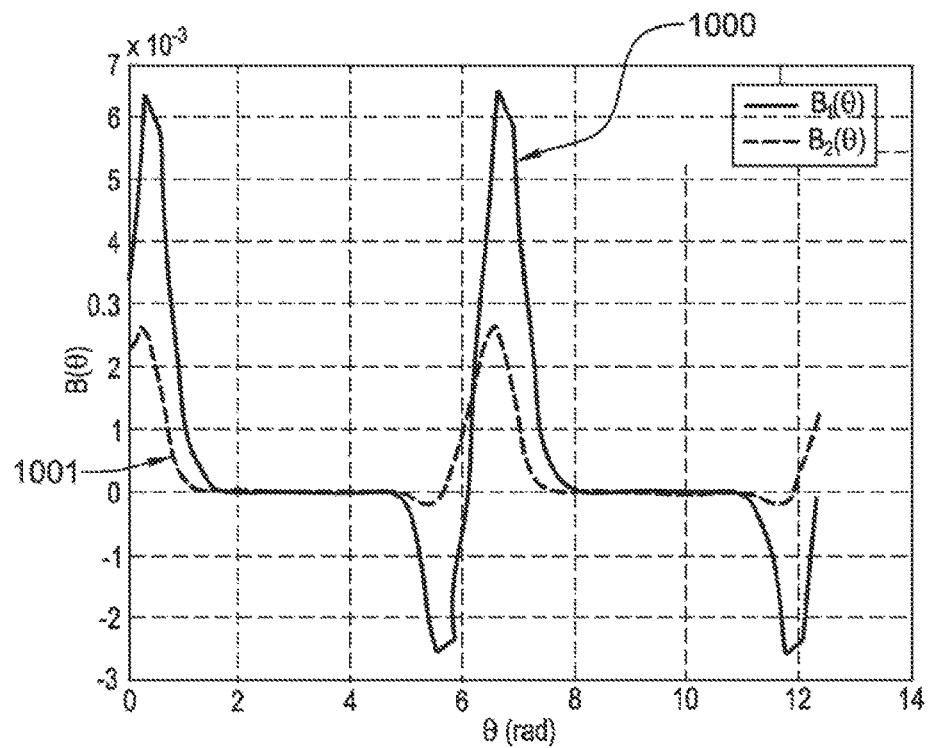
FIG. 10A illustrates the family of B(Θ) from an LPV model obtained using data generated from the *Neurospora* circadian model, in accordance with one or more aspects of the present invention.
Figure 10B:
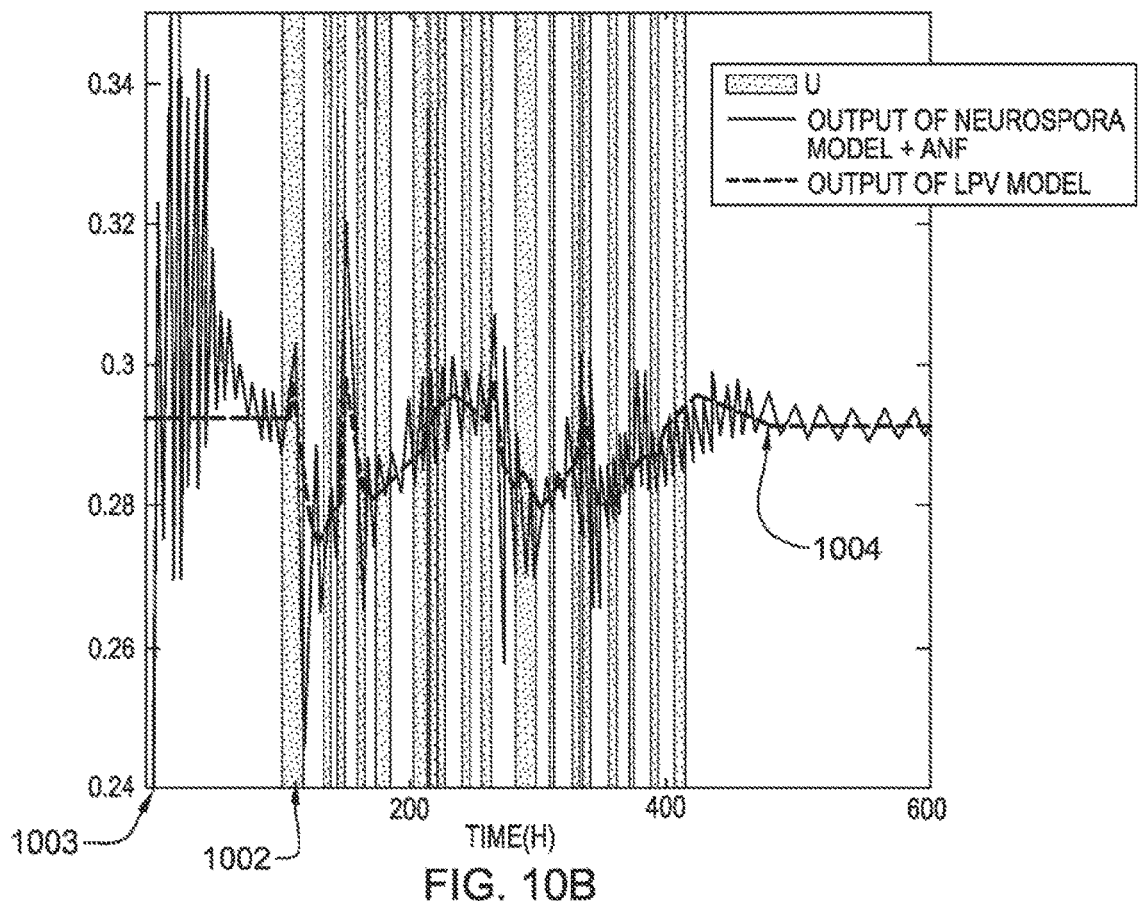
FIG. 10B illustrates the ability of the LPV model to predict the circadian phase response using the Neurosproa circadian model for simulation, in accordance with one or more aspects of the present invention.

FIGS. 10A & 10B illustrate the identification result using the biomolecular circadian rhythm model for *neurospora* described in P. Francois, "A Model for the *Neurospora* Circadian Clock", Biophysical Journal, Volume 88, pages 2369-2283, April 2005. For the *Neurospora* Model, the two components of the identified B(Θ) matrix are shown in FIG. 10A, and labeled 1000, 1001. The comparison of the identified model output for a given circadian light input 1002 shows the noisy adaptive circadian phase estimator result 1003 versus the identified LPV model output 1004.

As noted initially, the circadian phase estimate may be used together with the identified model to facilitate feedback control of the circadian light input to the subject, for instance, to entrain, adjust and/or otherwise regulate the circadian rhythm of the subject. Compared with existing methods of light-based circadian rhythm entrainment, the approach disclosed herein is adaptive, being based on estimated circadian phase of the subject, and light input to the subject, thus adapting to the characteristics of each individual subject. However, those skilled in the art should note from the description provided below that circadian rhythm regulation or control, in accordance with the concepts disclosed herein, could be employed in combination with any circadian rhythm phase estimation process.

Figure 11A:
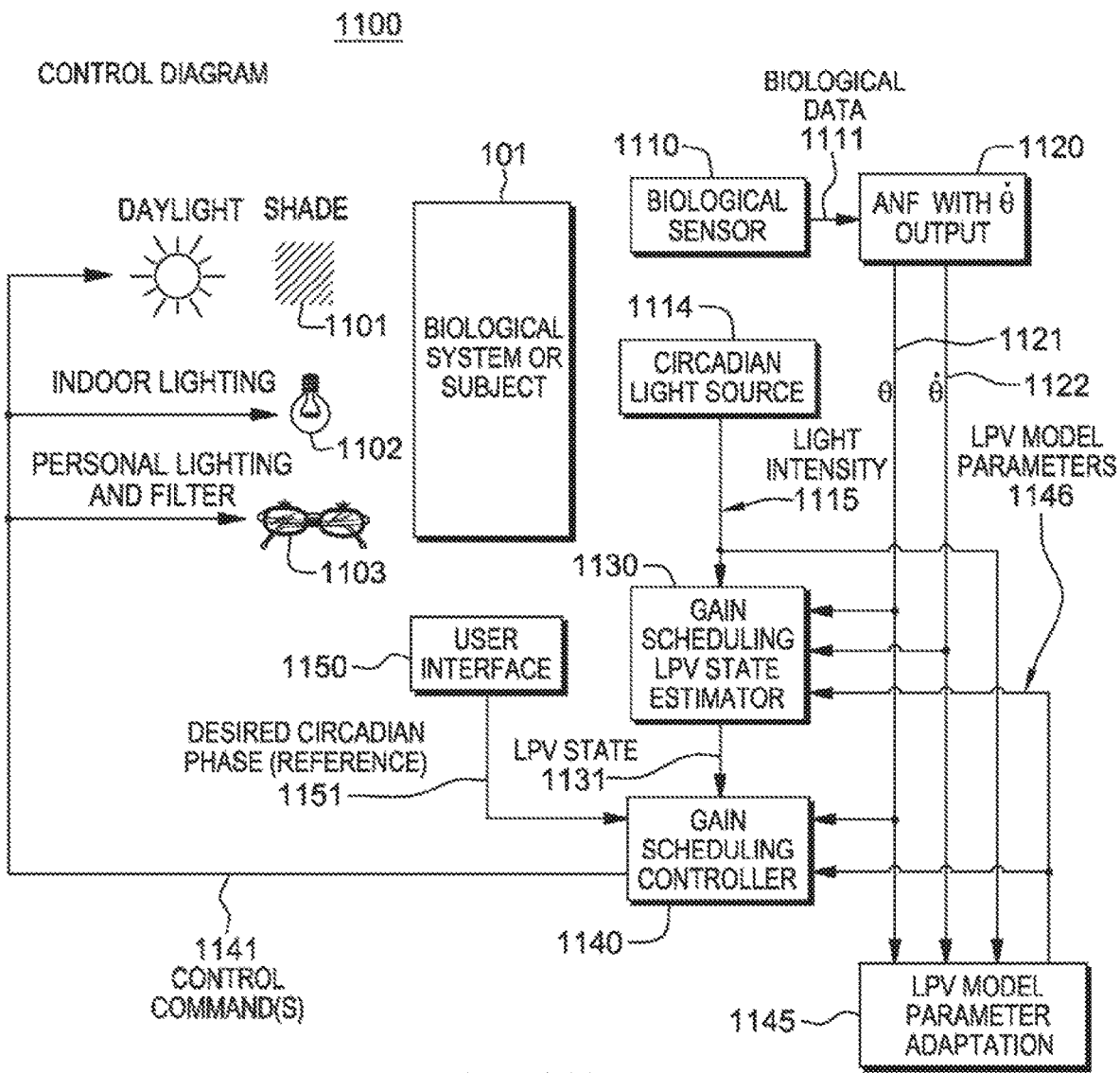
FIG. 11A depicts one embodiment of a system for regulating circadian rhythm of a subject, in accordance with one or more aspects of the present invention.

FIG. 11A depicts one embodiment of a circadian rhythm regulation (or control) system, generally denoted 1100, in accordance with one or more aspects of the present invention. A biological system or subject 101 whose circadian rhythm is to be regulated is, in one embodiment, equipped with one or more biological (or physiological) sensors 1110, with the biological signal (or data) 1111 output from biological sensors 1110 being processed by a circadian phase estimator 1120. In one embodiment, the circadian phase estimator employs an adaptive frequency tracking approach, such as described above in connection with the estimator embodiments of FIGS. 2A & 5A. In the embodiment of FIG. 11A, the circadian phase estimator 1120 outputs the estimated circadian phase (Θ) 1121, as well as its time derivative ( ) 1122. Commensurate with sensing biological data, circadian light intensity 1115 is measured or sensed by a circadian light sensor 1114, and the circadian phase estimate (Θ), circadian phase time derivative ( ), and circadian light intensity 1115 are used to periodically updated (in one embodiment) the LPV model parameters 1145.

In one embodiment, the model parameters are updated or adjusted to fit the data by minimizing the difference in the circadian phase output for the measured circadian light input. A user interface 1150 may be used to specify the desired circadian phase ($\Theta_r$) 1151. For example, for night-shift workers, an 8-hour phase advance may be desired, while for travelers over multiple time zones, a phase difference corresponding to the time zone difference may be desired.

A circadian phase controller 1140 compares the estimated circadian phase and the specified or desired circadian phase to adjust the circadian light input 1141 to the subject 101. One embodiment of controller 1140 is a gain-scheduling controller based on the above-described LPV model. In this embodiment, a family of LTI controllers may be designed based on the LTI systems in the LPV circadian phase model. The controllers are then combined together through interpolation of the circadian phase estimate, which is also the gain-scheduling parameter. The circadian phase controller (or gain-scheduling controller) 1140 requires the knowledge of the LPV state variable 1131. For each LTI system in the LPV model, a standard state estimator may be constructed, as would be understood by one skilled in the art. The estimator may be combined together through interpolation of the circadian phase estimate. The resulting state estimator is the gain-scheduling LPV state estimator 1130. The circadian light control command 1141 may be implemented using multiple forms of circadian light regulation. For instance, shades 1101 may be used to block ambient circadian light from, for instance, daylight, or LED or LCD displays. Ambient lighting 1102 may be controlled to the required circadian light intensity level, and/or personal lighting systems 1103 may be used to either block out undesired ambient light or inject required circadian light to the subject at the required level commanded by the control command signals 1141 provided by the circadian phase controller 1140.

Figure 11B:
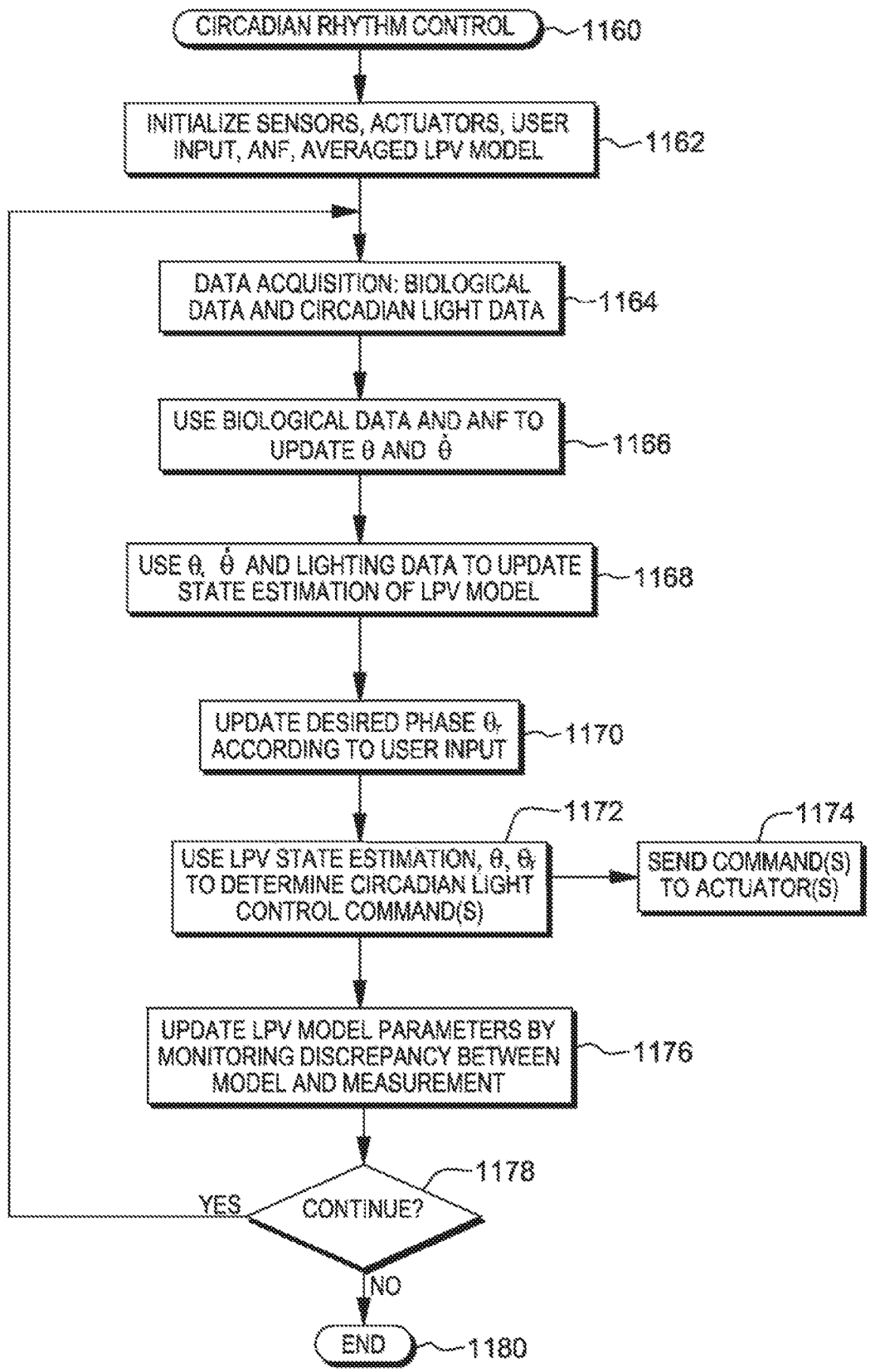
FIG. 11B depicts one embodiment of a process for circadian rhythm regulation utilizing, for instance, the circadian rhythm regulation system of FIG. 11A, in accordance with one or more aspects of the present invention.

FIG. 11B depicts one embodiment of a circadian phase control process employing a circadian phase regulation system such as described above in connection with FIG. 11A. Circadian rhythm control 1160 begins with initialization of the control system, including starting of biological and light sensors, starting actuators (i.e., for controlling light regulation devices), initializing the biological signal input, the circadian phase estimator, and the identified LPV model to be employed in phase regulation 1162. The biological data and circadian light data are acquired at regular intervals 1164, and the measured biological data and circadian phase estimator are used to update the circadian phase estimate ($\Theta$) and its time derivative ( ) 1166. The circadian phase ($\Theta$), its time derivative ( ), and the measured circadian light (u) are used to update the estimate of the state of the identified LPV model. The desired circadian phase ($\Theta_r$) is acquired at regular intervals, for instance, through a user interface 1170. The circadian phase estimate, the desired circadian phase, and the estimated state of the identified LPV model, are then used together within the circadian rhythm controller to generate one or more circadian light control commands 1172 for sending to the one or more circadian light control actuators 1174 of the circadian rhythm system. The LPV model parameters are updated to minimize the discrepancy between the LPV circadian phase output and the circadian phase estimate 1176. Processing then determines whether to continue with circadian rhythm regulation or to discontinue regulation 1178. In one example, processing may be discontinued via a user command or expiration of a pre-specified length of time. If control is continued, processing loops back to obtain a next set of data, including a next set of biological data and circadian light data 1164. Otherwise, circadian rhythm regulation ends, for instance, by entering a shutdown phase 1180.

Figure 12A:
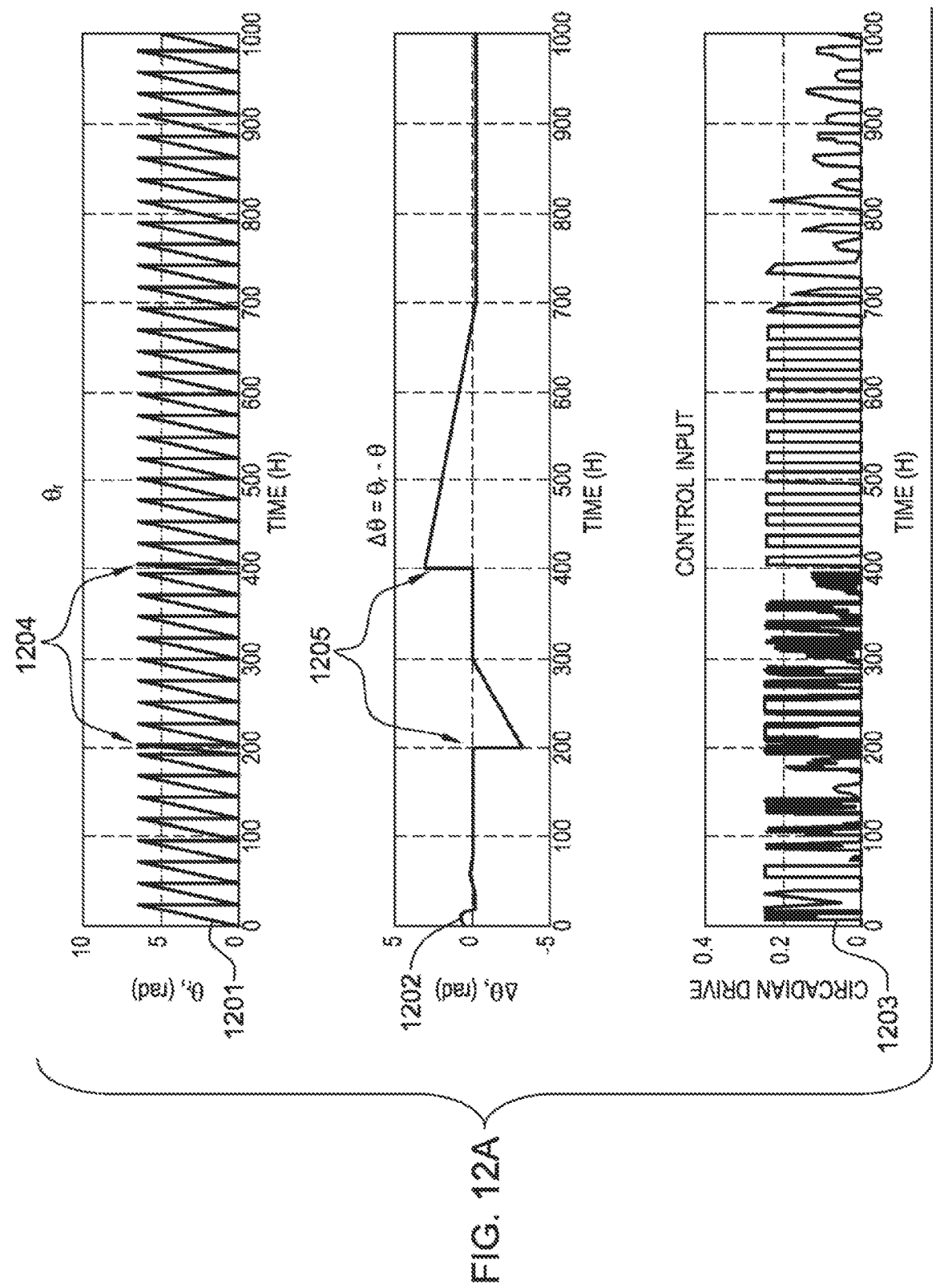
FIG. 12A illustrates an example of circadian rhythm control using the circadian rhythm regulation system of FIG. 11A, applied to a human circadian rhythm model, in accordance with one or more aspects of the present invention.
Figure 12B:
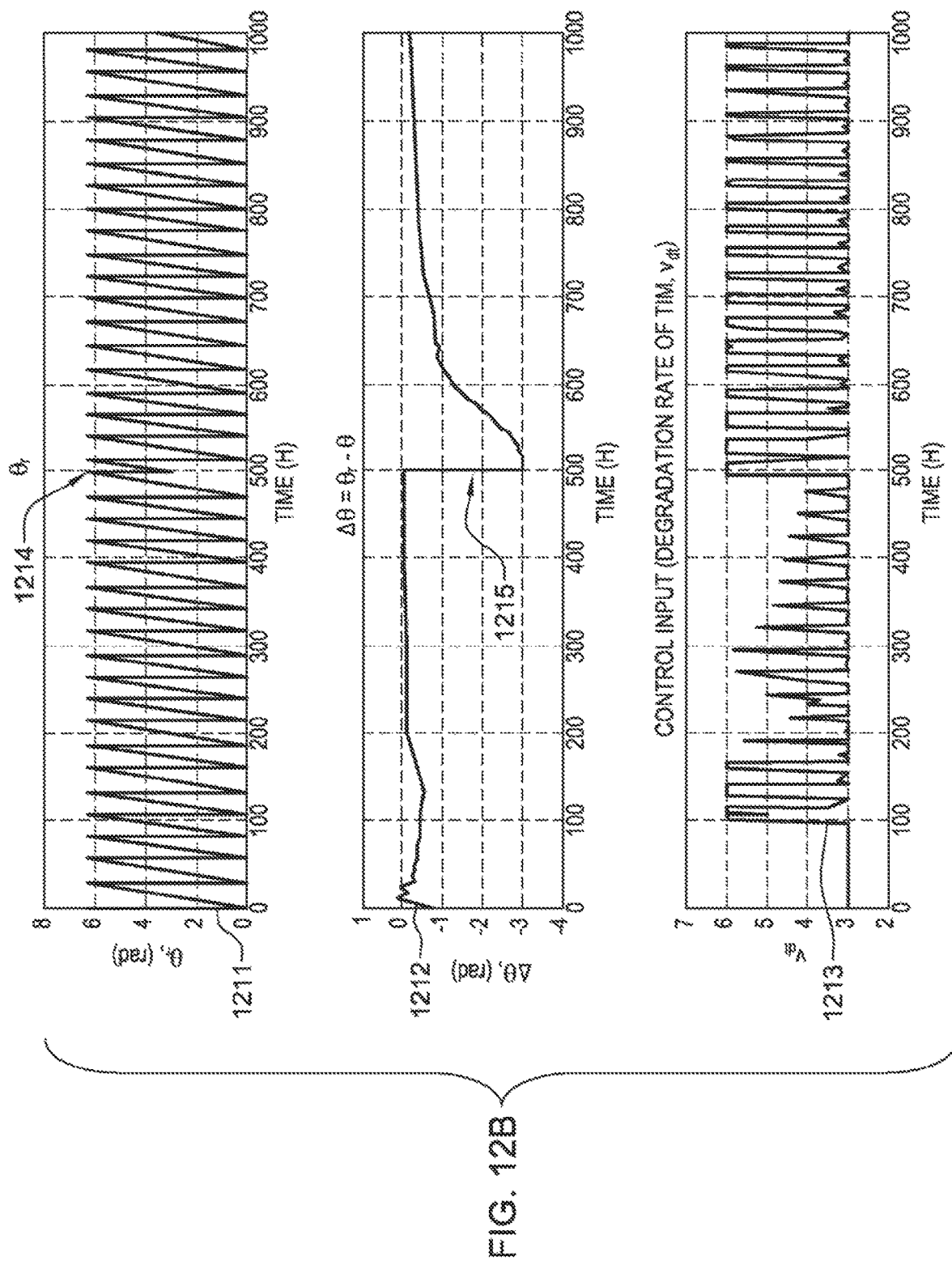
FIG. 12B illustrates an example of circadian rhythm control using the circadian rhythm regulation system of FIG. 11A, applied to a biomolecular circadian rhythm model for *drosophila*, in accordance with one or more aspects of the present invention.
Figure 12C:
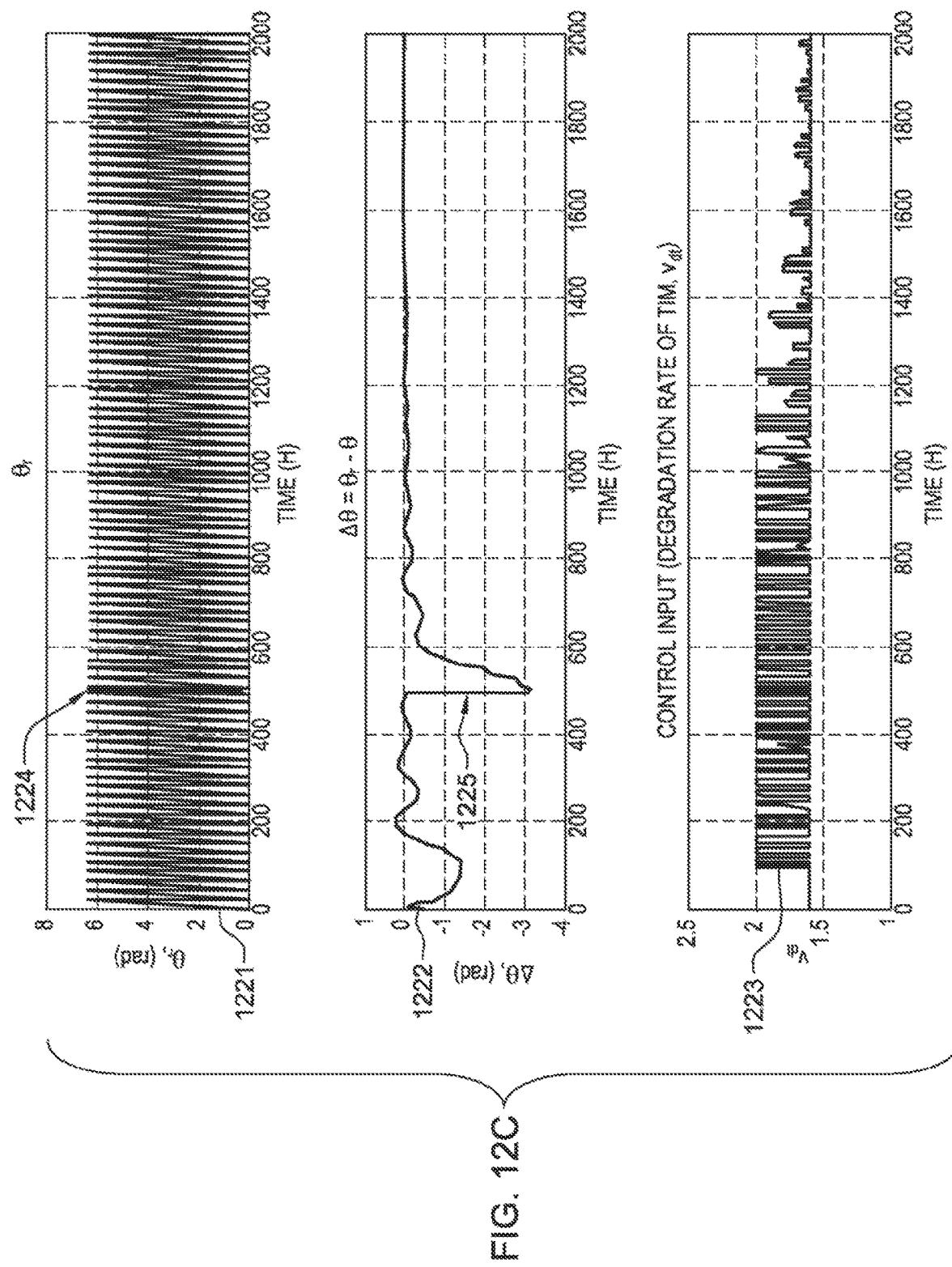
FIG. 12C depicts an example of circadian rhythm control using the circadian rhythm regulation system of FIG. 11A, applied to a biomolecular circadian rhythm model for *neurospora*, in accordance with one or more aspects of the present invention.

FIGS. 12A-12C illustrate the efficacy of the circadian phase control approach described herein when applied to three different simulation models. FIG. 12A illustrates control results using the above-referenced human circadian rhythm model developed by Kronauer et al., FIG. 12B illustrates the control results using the above-referenced biomolecular circadian rhythm model for *drosophila* described in J. C. Leloup et al., and FIG. 12C illustrates the control result using the above-referenced biomolecular circadian rhythm model for *neurospora*, described in P. Francis.

For the Kronauer Model, FIG. 12A depicts the circadian phase from the model 1201. In this example, at the $200^{th}$ hour, a phase delay of 12 hours is commanded (corresponding to $-\pi$ in terms of the circadian phase). At the $400^{th}$ hour, a phase advance of 12 hours is commanded to restore the original phase 1204. The controller is initially off until t=10 hours. The circadian phase difference 1202 between the commanded circadian phase and the actual circadian phase shows an initial transient difference. Once the controller is activated, the circadian phase difference is brought back to zero. At the $200^{th}$ hour, a $-\pi$ phase error is observed due the change of the circadian phase command. The controller is effective in bringing the phase difference back to zero by the $300^{th}$ hour 1205. At the $400^{th}$ hour, a $+\pi$ phase error occurs due to the change in the circadian phase command. The circadian phase controller is also effective in bringing this phase difference back to zero 1205, with the different circadian light inputs, from the controller, being depicted in 1203 as circadian drive versus time.

Referring to FIG. 12B, for the *Drosophila* Model, circadian phase from the model 1211 is shown. At the 500.sup.th hour (in this example), a phase delay of 12 hours is commanded (corresponding to a $-\pi$ in terms of circadian phase), as seen at 1214. The controller is initially off until time t=$100^{th}$ hour. The difference between the commanded circadian phase and the actual circadian phase shows an initial transient difference 1212, and once the controller is turned on, the circadian phase difference is brought back to zero. At the $500^{th}$ hour, a $-\pi$ phase error is observed 1215 due to the change of the circadian phase command. The controller is effective in brining the phase difference back to zero, with the circadian light input command 1213 from the controller also being depicted.

Referring to FIG. 12C, for the *Neurospora* Model, the circadian phase from the model 1221 is depicted. At the $500^{th}$ hour, in this example, a phase delay of 12 hours is assumed to be commanded (corresponding to $-\pi$ in terms of circadian phase), as illustrated 1224. The controller is initially off until time t=100th hour, and the difference between the commanded circadian phase and the actual circadian phase shows an initial transient difference 1222. Once the controller is turned on, the circadian phase difference is brought back to zero. At the $500^{th}$ hour, a-.pi. phase error is observed 1225 due to the change in the circadian phase command. The controller is effective in bringing the phase difference back to zero, with the circadian light input or command signal 1223 being depicted below the circadian phase difference signal.

Those skilled in the art will note from the above description that provided herein, in one aspect, are novel systems, methods and computer program products to facilitate estimating in real-time circadian phase of a subject, without use of a model. The estimating includes: obtaining a sensed biological signal measured or derived from the subject; and using, by one or more processors, adaptive frequency tracking to adaptively estimate the circadian phase of a subject from the individual subject's sensed biological signal. The adaptive frequency tracking may utilize single-harmonic or multi-harmonic filtering, with the single-harmonic or multi-harmonic filtering being a model-less process for adaptively estimating the circadian phase of the subject from the sensed biological signal or data for the subject. For instance, using adaptive frequency tracking may include ascertaining, by one or more processors, the circadian phase of the subject by determining a fundamental harmonic phase of the sensed biological signal from a set of internal variables provided by the single-harmonic or multi-harmonic filtering. The set of internal variables may include state variables for a first-order oscillator. Where the adaptive frequency tracking utilizes multi-harmonic filtering, the set of internal variables may include state variables for a higher-order oscillator.

In another aspect, the method may include adapting internal parameters used by the single-harmonic or multi-harmonic filtering, where the adapting utilizes a tracking error ascertained by comparing the sensed biological signal to filtered biological data determined by the single-harmonic or multi-harmonic filtering. The internal parameters may include a constant bias of the sensed biological signal and angular frequency of the circadian rhythm. Advantageously, adaptively estimating circadian phase of the subject, in accordance with this aspect of the present invention, occurs in real-time, and the adapting of the internal parameters used by the single-harmonic or multi-harmonic filtering occurs automatically.

In one implementation, the using by the processor(s) adaptive frequency tracking may include automatically using, by the one or more processors, a set of recursive, non-linear filters computed in real-time to adaptively estimate the circadian phase of the subject from the sensed biological signal for the subject. As a specific example, adaptive frequency tracking may utilize an adaptive notch filter, and the measured biological signal obtained from the subject can be represented as a linear combination of N harmonics and a DC component:

$$n = d^* + A_1^* \sin(\omega^* t + \phi_1) + A_2^* \sin(2\omega^* t + \phi_2) + \cdots + A_N^* \sin(N\omega^* t + \phi_N),$$

wherein internal variables of the adaptive frequency tracking converge to:

$$x_1 = \frac{A_1^* \cos(\omega^* t + \phi_1)}{2\zeta}$$

$$x_2 = \frac{A_1^* \omega \sin(\omega^* t + \phi_1)}{2\zeta}$$

$$x_3 = -\frac{A_2^* \cos(2\omega^* t + \phi_2)}{2\zeta}$$

$$x_2 = \frac{2A_2^* \cos(2\omega^* t + \phi_2)}{2\zeta}$$

$$\vdots$$

$$x_{2N-1} = -\frac{A_N^* \cos(N\omega^* t + \phi_N)}{2\zeta}$$

$$x_{2N} = \frac{NA_N^* \omega \sin(N\omega^* t + \phi_N)}{2\zeta}$$

$$d = d^*, \omega = \omega^*$$

and wherein the circadian phase of the subject comprises the phase of a fundamental harmonic defined as:

$$\theta = \tan^{-1} -\frac{x_2}{x_1 \omega}$$

where:
n=input, i.e., the sensed biological signal;
θ=output, i.e., the circadian phase estimate;
$x_1$, $x_2$=state variables for the $1^{st}$ order oscillator;
$x_3$, $x_4$=state variables for the $2^{nd}$ order oscillator;
$x_{2N-1}$, $x_{2N}$=state variables for the $N^{th}$ order oscillator;
d=estimated bias of the biological signal;
ω=estimated angular frequency of the circadian rhythm; and
ζ=notch width of the filter.

In another aspect, accelerating estimating of the circadian phase from the sensed biological signal is also provided herein via a feedback loop for the adaptive frequency tracking, where the feedback loop utilizes, in part, a circadian phase model to automatically ascertain a phase correction for the adaptive frequency tracking. In one embodiment, the feedback loop automatically determines a phase estimate discrepancy between a phase estimate of the adaptive frequency tracking and a phase estimate of the circadian phase model, and utilizes the phase estimate discrepancy to, in part, automatically determine the phase correction for the adaptive frequency tracking. The method may further include sensing circadian light exposure of the subject commensurate with sensing the biological signal of the subject, and the feedback loop may utilize the sensed circadian light exposure as input to the circadian phase model, and as input to, for instance, a tunable gain element, where the tunable gain element outputs a first phase correction signal as the phase correction for the adaptive frequency tracking, and a second phase correction signal for the circadian phase model. The first and second phase correction signals may be determined, in part, using the determined phase estimate discrepancy.

In another aspect, a light-based circadian rhythm model may be automatically determined or constructed for the subject using a linear parameter-varying system formulation, with sensed circadian light intensity as input, and the circadian phase of the subject as output. Note in this regard, that the circadian phase of the subject may be estimated or obtained using any available approach, with the above-summarized circadian phase estimation being one example of an approach which may be employed in connection with ascertaining a light-based circadian rhythm model, as described herein. The automatically constructing of the light-based circadian rhythm model may include: ascertaining multiple linear time-invariant models using multiple light profiles; transforming the multiple linear time-invariant models into observable canonical form; and combining the multiple linear time-invariant models into the light-based circadian rhythm model for the subject using the linear parameter-varying system formulation. In one example, the linear parameter-varying system formulation may be expressed as:

$$x_{k+1} = A(\theta_k)x_k + B(\theta_k)u_k$$

$$\dot{\theta}_k = Cx_k + \dot{\theta}_{k_{free\ running}}$$

where:
$x_{k+1}$=model state at time k+1;
$\theta_k$=the estimated circadian phase at time k;
$u_k$=the circadian light intensity at time k;
$\theta_{k_{free\ running}}$=free running circadian, phase when no circadian light is present;
C=a known constant matrix; and
$A(\theta_k)$, $B(\theta_k)$=matrices which are functions of $\theta_k$.

In a further aspect, a controller may use the automatically constructed, light-based circadian rhythm model for the subject in automatically adjusting light exposure of the subject to attain a desired circadian rhythm for the subject. In one implementation, the controller automatically generates a circadian light control command using the estimated circadian phase of the subject, a desired circadian phase for the subject, and an estimated state of the light-based circadian rhythm model. In addition, the method may include automatically updating parameters of the light-based circadian rhythm model to minimize discrepancy between the circadian phase output of the light-based circadian rhythm model and the estimated circadian phase.

As noted, aspects of the present invention can be used to facilitate adjusting a user's circadian pacemaker. Such adjustment can be useful towards, for instance, helping users improve sleep quality, reducing symptoms of jet lag, promoting earlier bedtimes, and/or reducing risks of diseases, such as cardiovascular disease, diabetes, obesity, and/or cancer. Aspects of the present invention can also be useful to cancer patients undergoing chemotherapy to increase the efficacy of treatment and reduce its side effects. Since humans do not have conscious access to the timing of their circadian pacemaker, the proposed device will serve as a tool to help treat non-pharmacologically those suffering from circadian disruption.

Aspects of the present invention may be used to determine, at any point in time, whether to recommend and/or apply a light stimulus or darkness, in order to facilitate adjusting a user's circadian pacemaker in a short amount of time. Some benefits, as noted above, are that the invention lends itself easily to changing constraints and conditions that are important to include for real-world applications such as people's work and travel schedules and daylight and darkness availability.

As will be appreciated by one skilled in the art, aspects of the present invention may be embodied as a system, method or computer program product. Accordingly, aspects of the present invention may take the form of an entirely hardware embodiment, an entirely software embodiment or an embodiment combining software and hardware aspects. Furthermore, aspects of the present invention may take the form of a computer program product embodied in one or more computer readable medium(s) having computer readable program code embodied thereon.

The computer readable medium may be a computer readable storage medium, such as, for instance, an electronic, magnetic, optical, electromagnetic, infrared or semiconductor system, apparatus, or device, or any combination thereof. More specific examples of the computer readable storage medium include for instance: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any combination thereof. In the context of this document, a computer readable storage medium may be any tangible or non-transitory medium that can contain or store program code for use by or in connection with an instruction execution system, apparatus, or device.

Program code embodied on a computer readable medium may be transmitted using an appropriate medium, including but not limited to wireless, wireline, optical fiber cable, RF, etc., or any combination thereof.

Computer program code for carrying out operations for aspects of the present invention may be written in any combination of one or more programming languages, including an object oriented programming language, such as Java, Smalltalk, C++ or the like, and conventional procedural programming languages, such as the "C" programming language, assembler or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the invention for various embodiments with various modifications as are suited to the particular use contemplated.

What is claimed is:

1. A method comprising:
estimating a circadian phase of the subject using a circadian rhythm control system to facilitate regulating a subject's circadian rhythm, the estimating comprising:
obtaining a sensed biological signal for the subject;
using, by one or more processors, adaptive frequency tracking to adaptively estimate the circadian phase of the subject from the sensed biological signal; and
the circadian rhythm control system initiating control of circadian light input to the subject based on the estimated circadian phase of the subject to regulate the subject's circadian rhythm,
wherein the adaptive frequency tracking utilizes an adaptive notch filter, and the measured biological signal obtained from the subject can be represented as a linear combination of N harmonics and a DC component:

$$n = d^* + A_1^* \sin(\omega^* t + \phi_1) + A_2^* \sin(2\omega^* t + \phi_2) + \ldots + A_N^* \sin(N\omega^* t + \phi_N)$$

wherein internal variables of the adaptive frequency tracking converge to:

$$x_1 = \frac{A_1^* \cos(\omega^* t + \phi_1)}{2\zeta}$$

$$x_2 = \frac{A_1^* \omega \sin(\omega^* t + \phi_1)}{2\zeta}$$

$$x_3 = -\frac{A_2^* \cos(2\omega^* t + \phi_2)}{2\zeta}$$

$$x_4 = \frac{2A_2^* \cos(2\omega^* t + \phi_2)}{2\zeta}$$

$$\vdots$$

$$x_{2N-1} = -\frac{A_N^* \cos(N\omega^* t + \phi_N)}{2\zeta}$$

$$x_{2N} = \frac{NA_N^* \omega \sin(N\omega^* t + \phi_N)}{2\zeta}$$

$$d = d^*, \omega = \omega^*$$

and wherein the circadian phase of the subject comprises the phase of a fundamental harmonic defined as:

$$\theta = \tan^{-1} - \frac{x_2}{x_1 \omega}$$

where
n=input, i.e., the sensed biological signal;
θ=output, i.e., the circadian phase estimate;
$x_1$, $x_2$=state variables for the $1^{st}$ order oscillator;
$x_3$, $x_4$=state variables for the $2^{nd}$ order oscillator;
$x_{2N-1}$, $x_{2N}$=state variables for the $N^{th}$ order oscillator;
d=estimated bias of the biological signal;
ω=estimated angular frequency of the circadian rhythm; and
ζ=notch width of the filter.

2. The method of claim 1, further comprising:
sensing circadian light intensity exposure of the subject commensurate with a sensing of the sensed biological signal of the subject; and
constructing a light-based circadian rhythm model for the subject using a linear parameter-varying system formulation with the sensed circadian light intensity as input and a model-based circadian phase of the subject as output.

3. The method of claim 2, further comprising using the light-based circadian rhythm model to ascertain and apply a phase correction to the adaptive frequency tracking providing the estimated circadian phase of the subject.

4. The method of claim 1, wherein the adaptive frequency tracking utilizes single-harmonic or multi-harmonic filtering, the single-harmonic or multi-harmonic filtering being a model-less process for adaptively estimating the circadian phase of the subject from the sensed biological signal for the subject.

5. The method of claim 4, wherein using adaptive frequency tracking comprises ascertaining, by the one or more processors, the circadian phase of the subject by determining a fundamental harmonic phase of the sensed biological signal from a set of internal variables provided by the single-harmonic or multi-harmonic filtering, the set of internal variables comprising state variables for a first or higher order oscillator.

6. The method of claim 5, further comprising adapting internal parameters used by the single-harmonic or multi-harmonic filtering, the adapting utilizing a tracking error ascertained by comparing the sensed biological signal to filtered biological data determined by the single-harmonic or multi-harmonic filtering, the internal parameters comprising at least one of a constant bias of the sensed biological signal or an angular frequency of circadian rhythm.

7. The method of claim 6, wherein adaptively estimating the circadian phase of the subject from the sensed biological signal occurs in real time, and adapting the internal parameters used by the single-harmonic or multi-harmonic filtering occurs automatically.

8. The method of claim 1, wherein the using by the one or more processors adaptive frequency tracking comprises using, by the one or more processors, a set of recursive, non-linear filters computed in real time to adaptively estimate the circadian phase of the subject from the sensed biological signal from the subject.

9. The method of claim 1, further comprising accelerating estimating of the circadian phase from the sensed biological signal by providing a feedback loop for the adaptive frequency tracking, the feedback loop utilizing, in part, the light-based circadian rhythm model, in ascertaining the phase correction for the adaptive frequency tracking.

10. The method of claim 9, wherein the feedback loop determines a phase estimate discrepancy between a phase estimate of the adaptive frequency tracking and a phase estimate of the circadian phase model, and utilizes the phase estimate discrepancy to, in part, determine the phase correction for the adaptive frequency tracking.

11. The method of claim 10, wherein the feedback loop utilizes the sensed circadian light exposure as input to the circadian rhythm model and as input to a tunable gain element, the tunable gain element outputting a first phase correction signal as the phase correction for the adaptive frequency tracking, the first phase correction signal being determined, in part, using the determined phase estimate discrepancy.

12. The method of claim 11, wherein the tunable gain element further outputs a second phase correction signal for the circadian phase model, the second phase correction signal being determined, in part, using the phase estimate of the adaptive frequency tracking and the phase estimate of the circadian phase model.

13. The method of claim 1, wherein the constructing comprises:
- ascertaining multiple linear time-invariant models using multiple light profiles;
- transforming the multiple linear time-invariant models into observable canonical form; and
- combining the multiple linear time-invariant models into the light-based circadian rhythm model for the subject using the linear parameter-varying system formulation.

14. The method of claim 1, wherein the linear parameter-varying system formulation comprises:

$$x_{k+1}=A(\theta_k)x_k+B(\theta_k)u_k$$

$$\dot{\theta}_k=Cx_k+\dot{\theta}_{k_{free\ running}}$$

where:
- $x_{k+1}$=model state at time (for $x_{k+1}$);
- $\theta_k$=the estimated circadian phase at time k;
- $u_k$=the circadian light intensity at time k;
- $\theta_{k_{free\ running}}$=free running circadian phase when no circadian light is present;
- C=a known constant matrix; and
- $A(\theta_k)$, $B(\theta_k)$=matrices which are functions of $\theta_k$.

15. A system comprising:
a circadian rhythm control system to facilitate regulating a subject's circadian rhythm, the circadian rhythm control system comprising one or more processors, which facilitate:
- obtaining a sensed biological signal for the subject;
- using, by the one or more processors, adaptive frequency tracking to adaptively estimate the circadian phase of the subject from the sensed biological signal; and
the circadian rhythm control system initiating control of circadian light input to the subject based on the estimated circadian phase of the subject to regulate the subject's circadian rhythm,
wherein the adaptive frequency tracking utilizes an adaptive notch filter, and the measured biological signal obtained from the subject can be represented as a linear combination of N harmonics and a DC component:

$$n=d^*+A_1^*\sin(\omega^*t+\phi_1)+A_2^*\sin(2\omega^*t+\phi_2)+\ldots+A_N^*\sin(N\omega^*t+\phi_N)$$

wherein internal variables of the adaptive frequency tracking converge to:

$$x_1 = \frac{A_1^*\cos(\omega^*t+\phi_1)}{2\zeta}$$

$$x_2 = \frac{A_1^*\omega\sin(\omega^*t+\phi_1)}{2\zeta}$$

$$x_3 = -\frac{A_2^*\cos(2\omega^*t+\phi_2)}{2\zeta}$$

$$x_2 = \frac{2A_2^*\cos(2\omega^*t+\phi_2)}{2\zeta}$$

$$\vdots$$

$$x_{2N-1} = -\frac{A_N^*\cos(N\omega^*t+\phi_N)}{2\zeta}$$

$$x_{2N} = \frac{NA_N^*\omega\sin(N\omega^*t+\phi_N)}{2\zeta}$$

$$d = d^*, \omega = \omega^*$$

and wherein the circadian phase of the subject comprises the phase of a fundamental harmonic defined as:

$$\theta = \tan^{-1} - \frac{x_2}{x_1\omega}$$

where
- n=input, i.e., the sensed biological signal;
- θ=output, i.e., the circadian phase estimate;
- $x_1$, $x_2$=state variables for the $1^{st}$ order oscillator;
- $x_3$, $x_4$=state variables for the $2^{nd}$ order oscillator;
- $x_{2N-1}$, $x_{2N}$=state variables for the $N^{th}$ order oscillator;
- d=estimated bias of the biological signal;
- ω=estimated angular frequency of the circadian rhythm; and
- ζ=notch width of the filter.

16. The system of claim 15, wherein the circadian rhythm control system further facilitates:
- sensing circadian light intensity exposure of the subject commensurate with a sensing of the sensed biological signal of the subject; and
- constructing a light-based circadian rhythm model for the subject using a linear parameter-varying system formulation with the sensed circadian light intensity as input and a model-based circadian phase of the subject as output.

17. The system of claim 16, wherein the circadian rhythm control system further facilitates:

using the light-based circadian rhythm model to ascertain and apply a phase correction to the adaptive frequency tracking providing the estimated circadian phase of the subject.

18. A computer program product for adaptively estimating circadian phase of a subject, the computer program product comprising:
a non-transitory computer-readable storage medium readable by one or more processors and storing instructions for execution by the one or more processors for performing a method comprising:
obtaining a sensed biological signal for the subject;
using adaptive frequency tracking to adaptively estimate the circadian phase of the subject from the sensed biological signal; and
initiating control of circadian light input to the subject based on the estimated circadian phase of the subject to regulate the subject's circadian rhythm,
wherein the adaptive frequency tracking utilizes an adaptive notch filter, and the measured biological signal obtained from the subject can be represented as a linear combination of N harmonics and a DC component:

$$n = d^* + A_1^* \sin(\omega^* t + \phi_1) + A_2^* \sin(2\omega^* t + \phi_2) + \ldots + A_N^* \sin(N\omega^* t + \phi_N)$$

wherein internal variables of the adaptive frequency tracking converge to:

$$x_1 = \frac{A_1^* \cos(\omega^* t + \phi_1)}{2\zeta}$$

$$x_2 = \frac{A_1^* \omega \sin(\omega^* t + \phi_1)}{2\zeta}$$

$$x_3 = -\frac{A_2^* \cos(2\omega^* t + \phi_2)}{2\zeta}$$

$$x_2 = \frac{2A_2^* \cos(2\omega^* t + \phi_2)}{2\zeta}$$

$$\vdots$$

$$x_{2N-1} = -\frac{A_N^* \cos(N\omega^* t + \phi_N)}{2\zeta}$$

$$x_{2N} = \frac{NA_N^* \omega \sin(N\omega^* t + \phi_N)}{2\zeta}$$

$$d = d^*, \omega = \omega^*$$

and wherein the circadian phase of the subject comprises the phase of a fundamental harmonic defined as:

$$\theta = \tan^{-1} - \frac{x_2}{x_1 \omega}$$

where
n=input, i.e., the sensed biological signal;
θ=output, i.e., the circadian phase estimate;
$x_1$, $x_2$=state variables for the $1^{st}$ order oscillator;
$x_3$, $x_4$=state variables for the $2^{nd}$ order oscillator;
$x_{2N-1}$, $x_{2N}$=state variables for the $N^{th}$ order oscillator;
d=estimated bias of the biological signal;
ω=estimated angular frequency of the circadian rhythm; and
ζ=notch width of the filter.

19. The computer program product of claim 18, wherein the non-transitory computer-readable storage medium store further instructions comprising:
sensing circadian light intensity exposure of the subject commensurate with a sensing of the sensed biological signal of the subject; and
constructing a light-based circadian rhythm model for the subject using a linear parameter-varying system formulation with the sensed circadian light intensity as input and a model-based circadian phase of the subject as output.

20. The computer program product of claim 19, wherein the non-transitory computer-readable storage medium store further instructions comprising:
using the light-based circadian rhythm model to ascertain and apply a phase correction to the adaptive frequency tracking providing the estimated circadian phase of the subject.

* * * * *